US008379945B2

(12) United States Patent
Hirota

(10) Patent No.: US 8,379,945 B2
(45) Date of Patent: Feb. 19, 2013

(54) OPTICAL APPARATUS FOR ACQUIRING STRUCTURE INFORMATION AND ITS PROCESSING METHOD OF OPTICAL INTERFERENCE SIGNAL

(75) Inventor: Kazuhiro Hirota, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 655 days.

(21) Appl. No.: 12/646,788

(22) Filed: Dec. 23, 2009

(65) Prior Publication Data

US 2010/0166282 A1 Jul. 1, 2010

(30) Foreign Application Priority Data

Dec. 26, 2008 (JP) ................................ 2008-334526

(51) Int. Cl.
*G06K 9/00* (2006.01)

(52) U.S. Cl. ........................................ 382/128; 382/254

(58) Field of Classification Search .................. 382/128, 382/131, 154, 190, 254; 356/496, 503, 511; 600/109, 160
See application file for complete search history.

(56) References Cited

U.S. PATENT DOCUMENTS

| | | | | |
|---|---|---|---|---|
| 5,954,650 | A | 9/1999 | Saito et al. | 600/425 |
| 7,519,096 | B2 | 4/2009 | Bouma et al. | 372/102 |
| 7,567,349 | B2 | 7/2009 | Tearney et al. | 356/479 |
| 2003/0028100 | A1 | 2/2003 | Tearney et al. | 600/431 |
| 2003/0103212 | A1 | 6/2003 | Westphal et al. | 356/479 |
| 2005/0168751 | A1 | 8/2005 | Horii et al. | 356/479 |
| 2006/0244973 | A1 | 11/2006 | Yun et al. | 356/511 |
| 2007/0167710 | A1 | 7/2007 | Unal et al. | 600/407 |
| 2007/0263227 | A1 | 11/2007 | Mujat et al. | 356/511 |
| 2008/0075375 | A1 | 3/2008 | Unal et al. | 382/243 |
| 2008/0181263 | A1 | 7/2008 | Bouma et al. | 372/20 |
| 2008/0204655 | A1 | 8/2008 | Kikawa et al. | 351/206 |
| 2008/0208525 | A1 | 8/2008 | Kikawa et al. | 702/172 |
| 2009/0027689 | A1 | 1/2009 | Yun et al. | 356/511 |
| 2009/0257461 | A1 | 10/2009 | Bouma et al. | 372/20 |

FOREIGN PATENT DOCUMENTS

| | | | |
|---|---|---|---|
| JP | 2000-131222 | A | 5/2000 |
| JP | 2007-510143 | A | 4/2007 |
| JP | 2008-206684 | A | 9/2008 |
| JP | 2008-209166 | A | 9/2008 |

OTHER PUBLICATIONS

Yu, et al., "High-speed optical frequency-domain imaging," Optics Express, vol. 11, Issue No. 22, pp. 2953-2963, Nov. 3, 2003.
European Search Report dated Apr. 23, 2010.

*Primary Examiner* — Andrew W Johns
(74) *Attorney, Agent, or Firm* — McGinn IP Law Group, PLLC

(57) ABSTRACT

An optical apparatus for acquiring structure information comprises an optical branching device which splits a light outputted from a wavelength-swept light source into a sampling light and a reference light; a scanning device which scans a subject having a layer structure with the sampling light; and an signal processing device which acquires optical structure information of the subject by processing an interference signal between a return light which is reflected or backscattered at the subject and the reference light which has propagated a predetermined optical path length; wherein the signal processing device includes: a layer information extraction device which extracts layer information of the subject based on the interference signal; a feature value calculation device which calculates a feature value of the layer information; and an enhanced layer-structure image construction device which constructs an enhanced layer-structure image in which the layer structure is enhanced based on the feature value.

34 Claims, 16 Drawing Sheets

OPTICAL APPARATUS FOR ACQUIRING STRUCTURE INFORMATION AND ITS PROCESSING METHOD OF OPTICAL INTERFERENCE SIGNAL

BACKGROUND OF THE INVENTION

1. Field of the Invention

The present invention relates to optical apparatuses for acquiring structure information and its processing method of optical interference signals, and particularly to an optical apparatus for acquiring structure information for acquiring structure information which, for example, can clearly visualize an image of muscularis mucosa and its processing method of optical interference signals.

2. Description of the Related Art

Recently, for example, in the field of medical care, optical coherence tomography (OCT) measurement has come to be used as a method of noninvasively obtaining a tomogram within a living body. OCT measurement has an advantage over ultrasonic measurement in that it has a one order of magnitude higher resolution of about 10 μm thereby enabling it to obtain a detailed tomogram within a living body. Moreover, it can obtain a three-dimensional tomogram by acquiring a plurality of images while shifting the position in the direction perpendicular to the tomogram.

Currently, there is need of acquiring a detailed tomogram of a living body for the purpose of cancer diagnosis and others. As a method for that, conventionally proposed is a "Time Domain OCT" in which light outputted from a low-coherence light source is scanned to obtain a tomogram for a subject (Japanese Patent Application Laid-Open No. 2000-131222.)

Moreover, recently a "Frequency Domain OCT" is utilized which is an improved OCT that has overcome the drawbacks of the "Time Domain OCT", that is, a non-optimal signal-to-noise ratio, a low imaging frame rate, and a poor penetration depth (observation depth) (National Publication of International Patent Application No. 2007-510143 and "High-speed optical frequency-domain imaging," Optics Express, Vol. 11, Issue 22, pp. 2953-2963.)

On the other hand, the Frequency Domain OCT is utilized in other diagnostics fields and widely applied to clinical cases.

Further, as for OCT tomographic images, there is disclosed a technique in which after performing preprocessing (smoothing and averaging processing, etc.) to image data, a differential filter is applied in the depth direction to determine the pixel position corresponding to the layer boundary (Japanese Patent Application Laid-Open No. 2008-206684 and Japanese Patent Application Laid-Open No. 2008-209166).

Examples of typical apparatus configurations for performing Frequency Domain OCT measurement include two types of apparatuses: an SD-OCT (Spectral Domain OCT) apparatus and an SS-OCT (Swept Source OCT) apparatus.

An SD-OCT apparatus is configured such that: using a wideband low-coherent light such as an SLD (Super Luminescence Diode) light source, an ASE (Amplified Spontaneous Emission) light source, and white light as the light source, the wideband low-coherent light is split into a sampling light and a reference light; thereafter the sampling light is irradiated onto a measuring object to cause the reflected light which returns in that occasion and the reference light to interfere with each other; then the interference light is decomposed into each frequency component using a spectrometer so that the interference light intensity for each frequency component is measured using a detector array in which elements such as photo diodes are arranged in an array; and a Fourier transformation of the resulting spectrum interference intensity signals is performed by a computer, thus making up an optical tomographic image.

On the other hand, an SS-OCT apparatus is configured such that a laser of which optical frequency is swept in time is used as the light source to cause a reflected light and a reference light to interfere with each other at each wavelength so that the temporal waveform of the signal corresponding to the temporal change of the optical frequency is measured, and Fourier transformation of the resulting spectral interference intensity signal is performed by a computer, thus making up an optical tomographic image.

By the way, although OCT measurement is, as described above, a method to acquire an optical tomogram of a specific region, under an endoscope, it can discern to what extent the cancer-affected portion infiltrates, for example, by finding out a cancer-affected portion through observation by a ordinary illumination light endoscope and a special light endoscope and performing OCT measurement of that region. Further, by two-dimensionally scanning the optical axis of the sampling light, it is possible to acquire three-dimensional information in conjunction with the depth information by OCT measurement.

By the fusion of OCT measurement and three-dimensional computer graphic technology, it becomes possible to display a three-dimensional structure model made up of structure information of a measuring object with a resolution of the order of micrometers, and therefore the three dimensional structure model by OCT measurement is hereafter referred to as an optical three-dimensional structure image.

SUMMARY OF THE INVENTION

Generally in cancer diagnosis, whether or not the cancer invades, for example, the muscularis mucosa significantly affects the treatment policy; however, a problem exists in an OCT of related art, such as described in "High-speed optical frequency-domain imaging," Optics Express, Vol. 11, Issue 22, pp. 2953-2963, that the intensity of the reflected light is displayed by using only a gray scale and an indexed color, and therefore is difficult to distinguish.

On the other hand, in the related arts of Japanese Patent Application Laid-Open No. 2008-206684 and Japanese Patent Application Laid-Open No. 2008-209166, which are used in the ophthalmologic field, visualization of the layer structure of the eye ground is performed; in this type of diagnostic field, since the observation is made in a range in which observation depth is relatively small, even when image data after being transformed into an image is subjected to processing such as smoothing and averaging, the layer structure can be easily visualized. However, in an OCT for a digestive organ for which visualization of, for example, a muscularis mucosa which exists at a deep site is required, since the signal-to-noise ratio is poor at the deep area, it is difficult to visualize the muscularis mucosa by a similar technique.

The present invention has been made in view of the above described circumstances, and its object is to provide an optical apparatus for acquiring structure information which can acquire layer structure information which can identify a desired layer in a subject having a layer structure, and its processing method of optical interference signals.

In order to achieve the above described objects, the optical apparatus for acquiring structure information according to a first aspect of the present invention is an optical apparatus for acquiring structure information which splits light outputted from a wavelength-swept light source into a sampling light and a reference light, scans a subject having a layer structure with the sampling light, and acquires a structure information of the subject based on an interference signal between a return light which is reflected or backscattered at the subject and the reference light which has propagated a predetermined optical path length, the optical apparatus for acquiring structure information being configured to include: a layer information extraction device which extracts layer information of the subject based on the interference signal; a feature value calculation device which calculates a feature value of the layer information; and an enhanced layer-structure image construction device which constructs an enhanced layer-structure image in which the layer structure is enhanced based on the feature value.

In the optical apparatus for acquiring structure information according to the first aspect, it becomes possible to acquire layer structure information which can identify a desired layer in a subject having a layer structure as the result of that the layer information extraction device extracts layer information of the subject based on the interference signal, the feature value calculation device calculates a feature value of the layer information, and further the enhanced layer-structure image construction device constructs an enhanced layer-structure image in which the layer structure is enhanced based on the feature value.

As described in the optical apparatus for acquiring structure information according to the second aspect of the present invention, it is preferable that in the optical apparatus for acquiring structure information according to the first aspect, the layer information extraction device is made up of a Fourier transformation device (410) which performs Fourier transformation of the interference signal to extract the layer information, and the feature value calculation device is made up of a differentiation processing device which calculates a differential value resulting from differentiation of the layer information, as the feature value.

As described in the optical apparatus for acquiring structure information according to the third aspect of the present invention, it is preferable that the optical apparatus for acquiring structure information according to the second aspect, further comprises: a layer-information noise component removal device which removes a noise component of the layer information; and a feature-value noise component removal device which removes a noise component of the feature value, wherein the differentiation processing device calculates a differential value resulting from the differentiation of the layer information from which the noise component is removed, as the feature value, and the enhanced layer-structure image construction device constructs the enhanced layer-structure image based on the feature value from which the noise component is removed.

As described in the optical apparatus for acquiring structure information according to the fourth aspect of the present invention, it is preferable that in the optical apparatus for acquiring structure information according to the third aspect, the layer-information noise component removal device is made up of a logarithmic-transformation smoothing device which performs logarithmic transformation and smoothing of the layer information to remove the noise component; and the feature-value noise component removal device is made up of a feature value smoothing processing device which performs smoothing of the feature value to remove the noise component.

As described in the optical apparatus for acquiring structure information according to the fifth aspect of the present invention, it is preferable that in the optical apparatus for acquiring structure information according to the fourth aspect, the logarithmic-transformation smoothing device performs smoothing of the layer information by any one of a frame averaging processing device, a line averaging processing device, and a moving averaging processing device.

As described in the optical apparatus for acquiring structure information according to the sixth aspect of the present invention, it is preferable that in the optical apparatus for acquiring structure information according to the fifth aspect, the frame averaging processing device performs averaging of the layer information between multiple frames by using any one of the processings of simple averaging, weighted averaging, and recursive frame correlation.

As described in the optical apparatus for acquiring structure information according to the seventh aspect of the present invention, it is preferable that in the optical apparatus for acquiring structure information according to the fifth or sixth aspect, the line averaging processing device performs averaging of the signal between multiple lines by using one of the processings of simple averaging and a weighted averaging.

As described in the optical apparatus for acquiring structure information according to the eighth aspect of the present invention, it is preferable that in the optical apparatus for acquiring structure information according to any one of the fifth to seventh aspects, the moving averaging processing device performs smoothing of the signal in the depth direction by using any one of a simple moving average, a weighted moving average, and a lowpass filter.

As described in the optical apparatus for acquiring structure information according to the ninth aspect of the present invention, it is preferable that in the optical apparatus for acquiring structure information according to any one of the fourth to eighth aspects, the feature value smoothing processing device performs smoothing of the feature value of the subject in the depth direction by using any one of a simple moving average, a weighted moving average, and a lowpass filter.

As described in the optical apparatus for acquiring structure information according to the tenth aspect of the present invention, it is preferable that in the optical apparatus for acquiring structure information according to any one of the fourth to eighth aspects, the logarithmic-transformation smoothing device is made up of a logarithmic transformation device which performs logarithmic transformation of the layer information, and a smoothing device which performs smoothing of the logarithmically transformed layer information.

As described in the optical apparatus for acquiring structure information according to the eleventh aspect of the present invention, it is preferable that in the optical apparatus for acquiring structure information according to any one of the fourth to eighth aspects, the logarithmic-transformation smoothing device is made up of a smoothing device which performs smoothing of the logarithmically transformed layer information and a logarithmic transformation device which performs logarithmic transformation of the smoothed layer information.

As described in the optical apparatus for acquiring structure information according to the twelfth aspect of the present invention, it is preferable that in the optical apparatus for acquiring structure information according to any one of the fourth to eleventh aspects, the enhanced layer-structure image construction device compares the feature value with a predetermined threshold and constructs an enhanced layer-structure image in which the layer structure is enhanced based on the comparison result.

As described in the optical apparatus for acquiring structure information according to the thirteenth aspect of the present invention, it is preferable that in the optical apparatus for acquiring structure information according to any one of the fourth to twelfth aspects, the enhanced layer-structure image construction device constructs an enhanced layer-structure image in which the layer structure is enhanced according to a predetermined color map, as a color image.

As described in the optical apparatus for acquiring structure information according to the fourteenth aspect of the present invention, it is preferable that in the optical apparatus for acquiring structure information according to any one of the first to third aspects, the enhanced layer-structure image construction device compares the feature value with a predetermined threshold and constructs an enhanced layer-structure image in which the layer structure is enhanced based on the comparison result.

As described in the optical apparatus for acquiring structure information according to the fifteenth aspect of the present invention, it is preferable that in the optical apparatus for acquiring structure information according to any one of the first to third aspects, or fourteenth aspect, the enhanced layer-structure image construction device constructs an enhanced layer-structure image in which the layer structure is enhanced according to a predetermined color map, as a color image.

As described in the optical apparatus for acquiring structure information according to the sixteenth aspect of the present invention, the optical apparatus for acquiring structure information according to any one of the fourth to thirteenth aspects may be configured to further include: a layer-structure image construction device which constructs a layer structure image from the layer information which is logarithmically transformed by the logarithmic-transformation smoothing device, and an image synthesis device which synthesizes the layer structure image with the enhanced layer-structure image.

As described in the optical apparatus for acquiring structure information according to the seventeenth aspect of the present invention, it is preferable that in the optical apparatus for acquiring structure information according to the sixteenth aspect, the image synthesis device adds together and synthesizes the layer structure image with the enhanced layer-structure image at a predetermined proportion.

The processing method of an optical interference signal of an optical apparatus for acquiring structure information according to the eighteenth aspect of the present invention is a processing method of an optical interference signal of an optical apparatus for acquiring structure information which splits a light outputted from a wavelength-swept light source into a sampling light and a reference light, scans a subject having a layer structure with the sampling light, and acquires optical structure information of the subject based on an interference signal between a return light which is reflected or backscattered at the subject and the reference light which has propagated a predetermined optical path length, wherein the processing method of an optical interference signal of an optical apparatus for acquiring structure information is configured to include: a layer information extraction step for extracting the layer information of the subject based on the interference signal; a feature value calculating step for calculating a feature value of the layer information; and an enhanced layer-structure image construction step for constructing an enhanced layer-structure image in which the layer structure is enhanced based on the feature value.

In the processing method of an optical interference signal of an optical apparatus for acquiring structure information according to the eighteenth aspect, it becomes possible to acquire layer structure information which can identify a desired layer in a subject having a layer structure as the result of that the layer information extraction step extracts layer information of the subject based on the interference signal, the feature value calculation step calculates a feature value of the layer information, and further the enhanced layer-structure image construction step includes constructing an enhanced layer-structure image in which the layer structure is enhanced based on the feature value.

As described in the processing method of an optical interference signal of an optical apparatus for acquiring structure information according to the nineteenth aspect of the present invention, it is preferable that in the processing method of an optical interference signal of an optical apparatus for acquiring structure information according to the eighteenth aspect, the layer information extraction step is made up of a Fourier transformation step for performing Fourier transformation of the interference signal to extract the layer information, and the feature value calculation step is made up of a differential processing step for calculating a differential value resulting from differentiation of the layer information, as the feature value.

As described in the processing method of an optical interference signal of an optical apparatus for acquiring structure information according to the twentieth aspect of the present invention, it is preferable that the processing method of an optical interference signal of an optical apparatus for acquiring structure information according to the nineteenth aspect further includes: a layer-information noise component removal step for removing a noise component of the layer information; and a feature-value noise component removal step for removing a noise component of the feature value, wherein the differential processing step includes calculating a differential value resulting from the differentiation of the layer information from which the noise component is removed, as the feature value, and the enhanced layer-structure image construction step includes constructing the enhanced layer-structure image based on the feature value from which the noise component is removed.

As described in the processing method of an optical interference signal of an optical apparatus for acquiring structure information according to the twenty-first aspect of the present invention, it is preferable that in the processing method of an optical interference signal of an optical apparatus for acquiring structure information according to the twentieth aspect, the layer-information noise component removal step is made up of a logarithmic transformation smoothing step for performing logarithmic transformation and smoothing of the layer information to remove the noise component; and the feature-value noise component removal step is made up of a feature value smoothing processing step for performing smoothing of the feature value to remove the noise component.

As described in the processing method of an optical interference signal of an optical apparatus for acquiring structure information according to the twenty-second aspect of the present invention, it is preferable that in the processing method of an optical interference signal of an optical apparatus for acquiring structure information according to the twenty-first aspect, the logarithmic transformation smoothing step performs smoothing of the layer information by any one of the steps of frame averaging processing, line averaging processing, and moving averaging processing.

As described in the processing method of an optical interference signal of an optical apparatus for acquiring structure information according to the twenty-third aspect of the present invention, it is preferable that in the processing method of an optical interference signal of an optical apparatus for acquiring structure information according to the twenty-second aspect, the frame averaging processing step performs smoothing of the layer information between multiple frames by using any one of the processings of simple averaging, weighted averaging, and recursive frame correlation.

As described in the processing method of an optical interference signal of an optical apparatus for acquiring structure information according to the twenty-fourth aspect of the present invention, it is preferable that in the processing method of an optical interference signal of an optical apparatus for acquiring structure information according to the twenty-second or twenty-third aspect, the line averaging processing step includes performing averaging of the signal between multiple lines by using either one of the processings of simple averaging and weighted averaging.

As described in the processing method of an optical interference signal of an optical apparatus for acquiring structure information according to the twenty-fifth aspect of the present invention, it is preferable that in the processing method of an optical interference signal of an optical apparatus for acquiring structure information according to any one of the twenty-second to twenty-fourth aspects, the moving averaging processing step includes performing smoothing of the signal in the depth direction by using any one of a simple moving average, a weighted moving average, and a lowpass filter.

As described in the processing method of an optical interference signal of an optical apparatus for acquiring structure information according to the twenty-sixth aspect of the present invention, it is preferable that in the processing method of an optical interference signal of an optical apparatus for acquiring structure information according to any one of the twenty-first to the twenty-fifth aspects, the feature value smoothing processing step includes performing smoothing of the feature value of the subject in the depth direction by using any one of a simple moving average, a weighted moving average, and a lowpass filter.

As described in the processing method of an optical interference signal of an optical apparatus for acquiring structure information according to the twenty-seventh aspect of the present invention, it is preferable that in the processing method of an optical interference signal of an optical apparatus for acquiring structure information according to any one the twenty-first to twenty-fifth aspects, the logarithmic transformation smoothing step is made up of a logarithmic transformation step for performing logarithmic transformation of the layer information, and a smoothing step for performing smoothing of the logarithmically transformed layer information.

As described in the processing method of an optical interference signal of an optical apparatus for acquiring structure information according to the twenty-eighth aspect of the present invention, it is preferable that in the processing method of an optical interference signal of an optical apparatus for acquiring structure information according to any one of the twenty-first to the twenty-fifth aspects, the logarithmic transformation smoothing step is made up of a smoothing step for performing smoothing of the layer information and a logarithmic transformation step for performing logarithmic transformation of the smoothed layer information.

As described in the processing method of an optical interference signal of an optical apparatus for acquiring structure information according to the twenty-ninth aspect of the present invention, it is preferable that in the processing method of an optical interference signal of an optical apparatus for acquiring structure information according to any one of the twenty-first to the twenty-eighth aspects, the enhanced layer-structure image construction step includes comparing the feature value with a predetermined threshold and constructing an enhanced layer-structure image in which the layer structure is enhanced based on the comparison result.

As described in the processing method of an optical interference signal of an optical apparatus for acquiring structure information according to the thirtieth aspect of the present invention, it is preferable that in the processing method of an optical interference signal of an optical apparatus for acquiring structure information according to any one of the twenty-first to the twenty-ninth aspects, the enhanced layer-structure image construction step includes constructing an enhanced layer-structure image in which the layer structure is enhanced according to a predetermined color map, as a color image.

As described in the processing method of an optical interference signal of an optical apparatus for acquiring structure information according to the thirty-first aspect of the present invention, it is preferable that in the processing method of an optical interference signal of an optical apparatus for acquiring structure information according to any one of the eighteenth to the twentieth aspects, the enhanced layer-structure image construction step includes comparing the feature value with a predetermined threshold and constructing an enhanced layer-structure image in which the layer structure is enhanced based on the comparison result.

As described in the processing method of an optical interference signal of an optical apparatus for acquiring structure information according to the thirty-second aspect of the present invention, it is preferable that in the processing method of an optical interference signal of an optical apparatus for acquiring structure information according to any one of the eighteenth to twentieth, and thirty-first aspects, the enhanced layer-structure image construction step includes constructing an enhanced layer-structure image in which the layer structure is enhanced according to a predetermined color map, as a color image.

As described in the processing method of an optical interference signal of an optical apparatus for acquiring structure information according to the thirty-third aspect of the present invention, the processing method of an optical interference signal of an optical apparatus for acquiring structure information according to any one of the twenty-first to thirtieth aspects may be configured to further include: a layer-structure image construction step for constructing a layer structure image from the layer information which is logarithmically transformed by the logarithmic transformation smoothing step; and an image synthesis step for synthesizing the layer structure image with the enhanced layer-structure image.

As described in the processing method of an optical interference signal of an optical apparatus for acquiring structure information according to the thirty-fourth aspect of the present invention, it is preferable that in the processing method of an optical interference signal of an optical apparatus for acquiring structure information according to the thirty-third aspect, the image synthesis step includes adding together and synthesizing the layer structure image with the enhanced layer-structure image at a predetermined proportion.

As described so far, the present invention can acquire layer structure information which can identify a desired layer in a subject having a layer structure.

DETAILED DESCRIPTION OF THE PREFERRED EMBODIMENTS

Hereafter, best modes for carrying out the present invention will be described.

First Embodiment

<External View of Imaging Diagnostic Apparatus>

Figure 1:
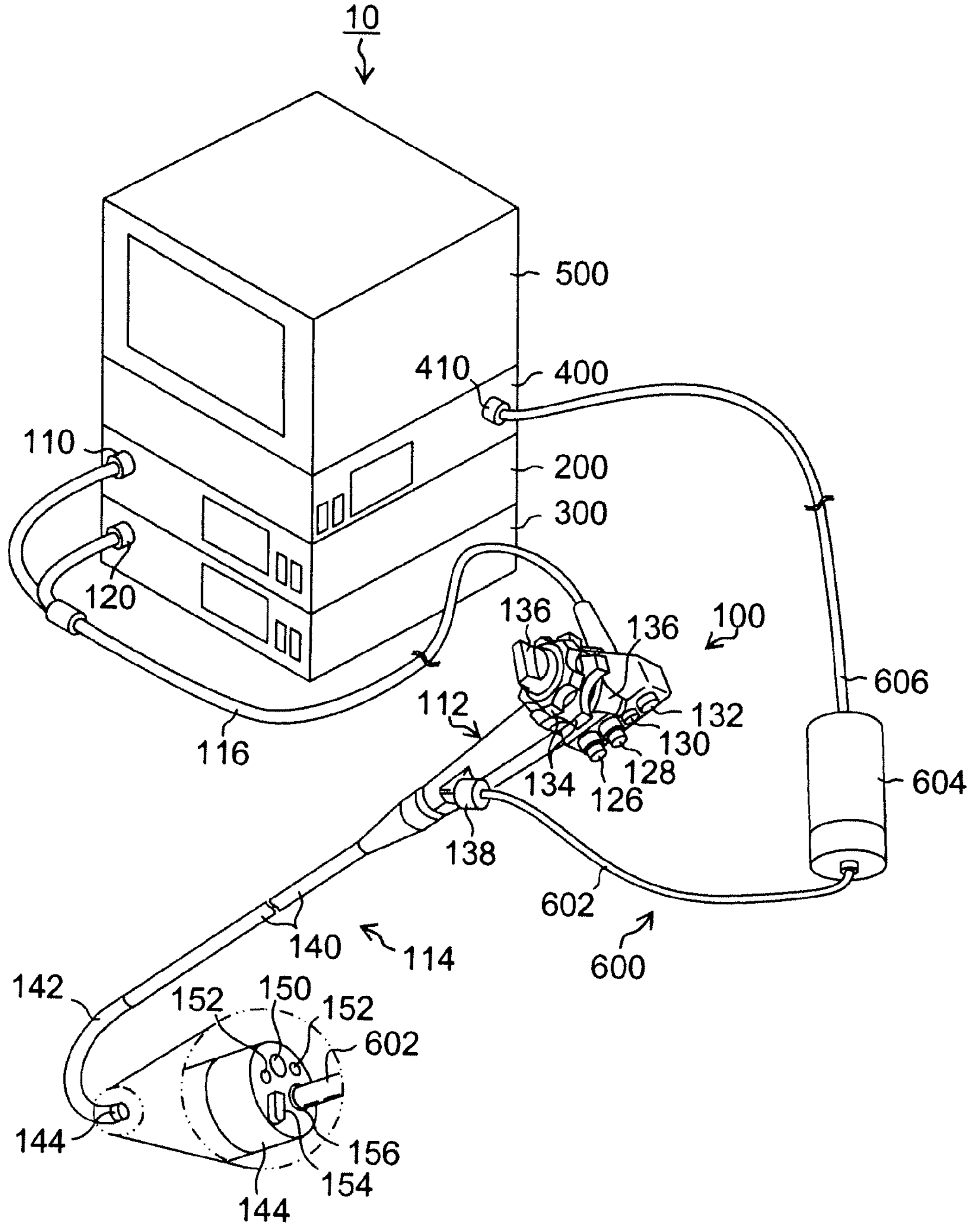
FIG. 1 is an external view to show an imaging diagnostic apparatus relating to a first embodiment of the present invention.

FIG. 1 is an external view to show an imaging diagnostic apparatus relating to a first embodiment of the present invention.

As shown in FIG. 1, an imaging diagnostic apparatus 10 is primarily made up of an endoscope 100, an endoscope processor 200, a light source apparatus 300, an OCT processor 400 as an optical apparatus for acquiring structure information of the present embodiment, and a monitor apparatus 500. It is noted that the endoscope processor 200 may be configured to incorporate the light source apparatus 300.

The endoscope 100 includes a hand operation part 112 and an insertion part 114 which is connected to the hand operation part 112. The operator manipulates the hand operation part 112 by grasping it and inserts the insertion part 114 into the body of a subject to make observation.

The hand operation part 112 is provided with a forceps insertion part 138, which is adapted to communicate with a forceps channel 156 of a tip end part 144. In the imaging diagnostic apparatus 10 relating to the present invention, an OCT probe 600 is inserted from the forceps insertion part 138 so that the OCT probe 600 is drawn out from a forceps channel 156. The OCT probe 600 is made up of: an insertion part 602 which is inserted from the forceps insertion part 138 and is drawn out from the forceps channel 156; an operation part 604 which is used by the operator to manipulates the OCT probe 600; and a cable 606 which is connected with the OCT processor 400 via a connector 410.

<Configurations of Endoscope, Endoscope Processor, and Light Source Apparatus>

[Endoscope]

The tip end part 144 of the endoscope 100 is arranged with an observation optics 150, an illumination optics 152, and a CCD (not shown).

The observation optics 150 causes an image of subject to be formed on a light receiving surface of a CCD which is not shown, and the CCD converts the image of subject formed on the light receiving surface into electric signals by each light receiving element. The CCD of the present embodiment is a color CCD in which color filters of the primary colors: red (R), green (G), and blue (B), are arranged in a predetermined array (a Bayer array, a honeycomb array, etc.) for each pixel.

[Light Source Apparatus]

The light source apparatus 300 causes visible light to enter into a light guide which is not shown. One end of the light guide is connected to the light source apparatus 300 via an LG connector 120 and the other end of the light guide is faced with the illumination optics 152. The light emitted from the light source apparatus 300 is released from the illumination optics 152 via the light guide to illuminate the visual range of the observation optics 150.

[Endoscope Processor]

The endoscope processor 200 receives an image signal outputted from the CCD via an electric connector 110. This analog image signal is converted into a digital image signal in the endoscope processor 200 and is subjected to necessary processing to be displayed on the screen of the monitor apparatus 500.

In this way, the data of an observed image obtained in the endoscope 100 is outputted to the endoscope processor 200 so that an image is displayed on the monitor apparatus 500 connected to the endoscope processor 200.

<Internal Configuration of OCT Processor and OCT Probe>

Figure 2:
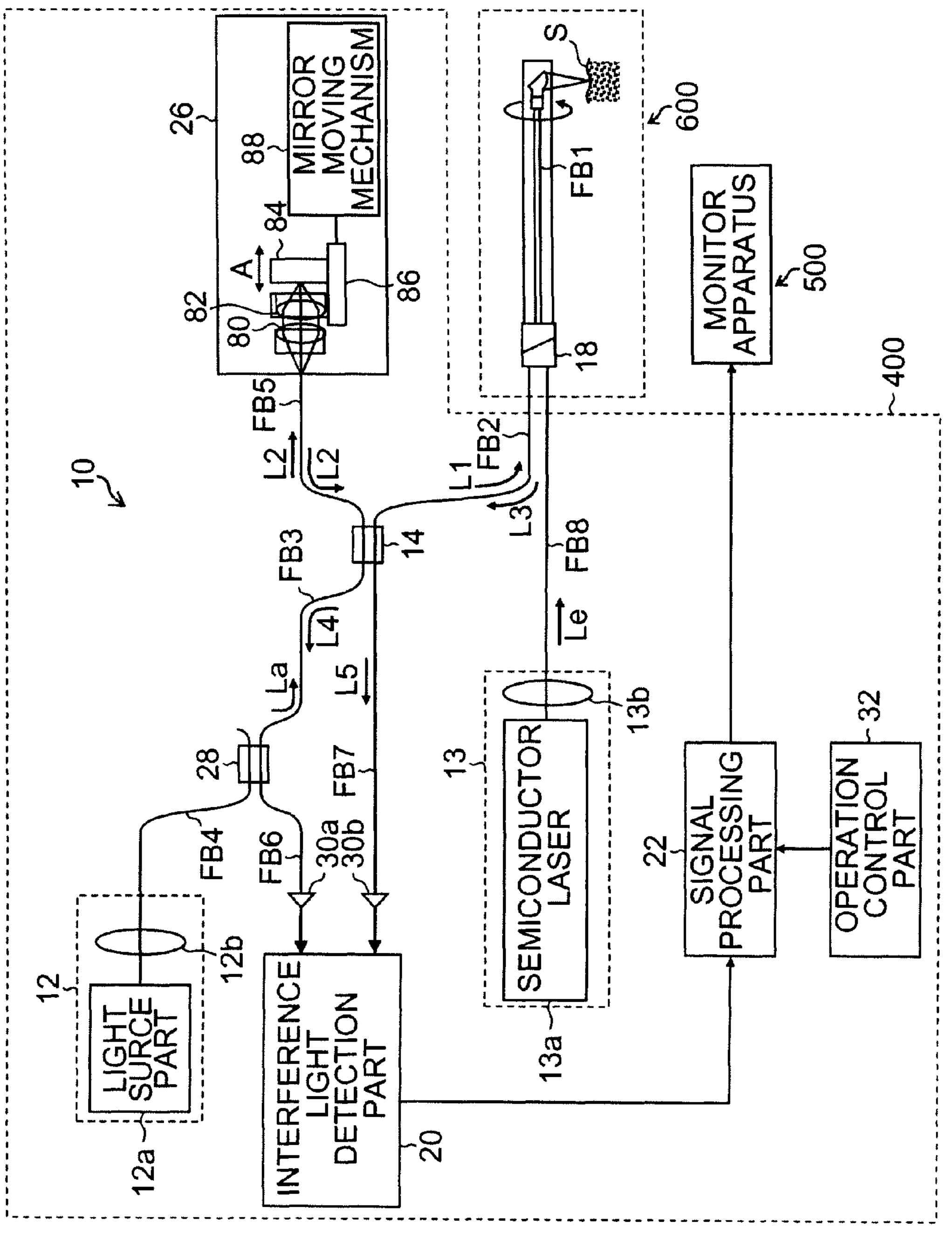
FIG. 2 is a block diagram to show the internal configuration of the OCT processor of FIG. 1.

FIG. 2 is a block diagram to show the internal configuration of the OCT processor of FIG. 1.

[OCT Processor]

The OCT processor 400 and the OCT probe 600 shown in FIG. 2, which are for the purpose of acquiring an optical tomographic image of a measuring object by an optical coherence tomography (OCT) measurement method, include: a first light source (a first light source unit) 12 which emits a light La for measurement; an optical fiber coupler (branching/combining part) 14 which makes the light La emitted from the first light source 12 to be branched into a sampling light (first light flux) L1 and a reference light L2 and combines a return light L3 from a measuring object S, which is a subject, with the reference light L2 to create an interference light L4; an OCT probe 600 including a rotary-side optical fiber FB1 which guides the sampling light L1 branched at the optical fiber coupler 14 to the measuring object and guides the return light L3 from the measuring object; a fixed-side optical fiber FB2 which guides the sampling light L1 to the rotary-side optical fiber FB1 and guides the return light L3 guided by the rotary-side optical fiber FB1; an optical connector 18 which rotatably connects the rotary-side optical fiber FB1 with the fixed-side optical fiber FB2 and transmits the sampling light L1 and the return light L3; an interference light detection part 20 which detects the interference light L4 produced at the optical fiber coupler 14 as an interference signal; and a processing part 22 which processes the interference signal detected by the interference light detection part 20 to acquire optical structure information. Further, based on the optical structure information acquired at the processing part 22, image is displayed on the monitor apparatus 500.

Further, the OCT processor 400 includes: a second light source (a second light source unit) 13 for emitting an aiming light (a second optical flux) L3 for indicating a mark for measurement; an optical-path-length adjustment part 26 which adjusts the optical path length of the reference light L2; detection parts 30*a* and 30*b* which detect return lights L4 and L5 combined at the optical fiber coupler 14; and an operation control part 32 which performs the change of input and setting of various conditions to the processing part 22.

It is noted that in the OCT processor 400 shown in FIG. 2, various optical fibers FB (FB3, FB4, FB5, FB6, FB7, FB8, etc.) including the rotary-side optical fiber FB1 and the fixed-side optical fiber FB2 are used as the optical path for guiding and transmitting various lights including the above described emitted light La, aiming light Le, sampling light L1, reference light L2, return light L3, etc. between components such as each optical device.

The first light source 12, which emits a light for OCT measurement (for example, a laser light or low coherence light of a wavelength of 1.3 μm), is a light source which emits a laser light La having a wavelength centered around 1.3 μm which is in an infrared region, while sweeping the frequency on a fixed cycle. The first light source 12 includes a light source 12*a* which emits a laser light or low coherence light La, and a lens 12*b* which condenses the light La emitted from the light source 12*a*. Further, though described in more detail later, the light La emitted from the first light source 12 is divided into the sampling light L1 and the reference light L2 at the optical fiber coupler 14 via the optical fibers FB4 and FB3, and the sampling light L1 is inputted into the optical connector 18.

Further, the second light source 13 is adapted to emit a visible light as the aiming light Le to facilitate the confirmation of the measuring site. For example, a red semiconductor laser light having a wavelength of 0.66 μm, a He—Ne laser light having a wavelength of 0.63 μm, and a blue semiconductor laser light having a wavelength of 0.405 μm, etc. may be used. Accordingly, the second light source 13 includes a semiconductor laser 13*a* which emits, for example, a red, blue, or green laser light and a lens 13*b* which condenses the aiming light Le emitted from the semiconductor laser 13*a*. The aiming light Le emitted from the second light source 13 is inputted into the optical connector 18 via an optical fiber FB8.

At the optical connector 18, the sampling light L1 and the aiming light Le are combined and guided to the rotary-side optical fiber FB1 within the OCT probe 600.

The optical fiber coupler (branching/combining part) 14 is made up of, for example, a 2-by-2 optical fiber coupler, and is optically connected respectively to the fixed-side optical fiber FB2, an optical fiber FB3, an optical fiber FB5, and an optical fiber FB7.

The optical fiber coupler 14 divides a light La which is inputted from the first light source 12 via the optical fibers FB4 and FB3 into a sampling light (first light flux) L1 and a reference light L2 so that the sampling light L1 is inputted into the fixed-side optical fiber FB2 and the reference light L2 is inputted into the optical fiber FB5.

Further, the optical fiber coupler 14 combines the light L2, which is inputted into the optical fiber FB5 and subjected to frequency shifting and change of optical path length by the below described optical-path-length adjustment part 26 thereafter being returned through the optical fiber FB5, with the light L3, which is acquired at the below described OCT probe 600 and guided from the fixed-side optical fiber FB2, and emits them to the optical fiber FB3 (FB6) and the optical fiber FB7.

The OCT probe 600 is connected with the fixed-side optical fiber FB2 via the optical connector 18 and the sampling light L1 combined with the aiming light Le is inputted into the rotary-side optical fiber FB 1 via the optical connector 18. The inputted sampling light L1 combined with the aiming light Le is transmitted by the rotary-side optical fiber FB 1 to be irradiated to a measuring object S. Then, the return light L3 from the measuring object S is acquired and the acquired return light L3 is transmitted by the rotary-side optical fiber FB1 to be emitted to the fixed-side optical fiber FB2 via the optical connector 18.

The optical connector 18 combines the sampling light (first light flux) L1 and the aiming light (second light flux) Le.

The interference light detection part 20 is connected with the optical fiber FB6 and the optical fiber FB7, and detects interference lights L4 and L5, which are created by combining the reference light L2 and the return light L3 at the optical fiber coupler 14, as the interference signal.

Here, the OCT processor 400 includes: a detection part 30*a* which is provided on the optical fiber FB6 branched from the optical fiber coupler 28, and detects the light intensity of the interference light L4; and a detection part 30*b* which detects the light intensity of the interference light L5 on the optical path of the optical fiber FB7.

The interference light detection part 20 generates interference signals based on the detection results of the detection part 30*a* and the detection part 30*b*.

The processing part 22 acquires optical structure information from the interference signal detected at the interference light detection part 20 to generate an optical three-dimensional structure image based on the acquired optical structure information, and outputs an image resulting from subjecting the optical three-dimensional structure image to various processing, to the monitor apparatus 500. The detailed configuration of the processing part 22 will be described later.

The optical-path-length adjustment part 26 is disposed at the side of emitting the reference light L3 of the optical fiber FB5 (that is, at the end of the optical fiber FB5 opposite to the optical fiber coupler 14).

The optical-path-length adjustment part 26 includes: a first optical lens 80 which collimates the light emitted from the optical fiber FB5; a second optical lens 82 which condenses the light collimated at the first optical lens 80; a reflection mirror 84 which reflects the light condensed at the second optical lens 82; a base 86 which supports the second optical lens 82 and the reflection mirror 84; and a mirror moving mechanism 88 which moves the base 86 in the direction parallel with the optical axis, and adjusts the optical path length of the reference light L2 by changing the distance between the first optical lens 80 and the second optical lens 82.

The first optical lens 80 collimates the reference light L2 emitted from the core of the optical fiber FB5 and condenses the reference light L2 reflected by the reflection mirror 84 into the core of the optical fiber FB5.

Further, the second optical lens 82 condenses the reference light L2 collimated by the first optical lens 80 onto the reflection mirror 84, and collimates the reference light L2 reflected by the reflection mirror 84. Thus, a confocal optics is formed by the first optical lens 80 and the second optical lens 82.

Further, the reflection mirror 84 is disposed at the focal point of the light condensed by the second optical lens 82 and reflects the reference light L2 condensed at the second optical lens 82.

This will result in that the reference light L2 emitted from the optical fiber FB5 is collimated and condensed onto the reflection mirror by the second optical lens 82. Thereafter, the reference light L2 reflected by the reflection mirror is collimated by the second optical lens 82 and condensed on the core of the optical fiber FB5 by the first optical lens 80.

Moreover, the base 86 secures the second optical lens 82 and the reflection mirror 84, and the mirror moving mechanism 88 moves the base 86 in the optical axis direction of the first optical lens 80 (the arrow A direction in FIG. 2).

Moving the base 86 in the arrow A direction by the mirror moving mechanism 88 can change the distance between the first optical lens 80 and the second optical lens 82 thereby adjusting the optical path length of the reference light L2.

The operation control part 32 as an extracting region setting device includes an input device such as a keyboard and a mouse, and a control device which controls various conditions based on input information, and is connected to the processing part 22. The operation control part 32 performs the input, setting, and change of various processing conditions in the processing part 22.

It is noted that the operation control part 32 may cause the monitor apparatus 500 to display an operation image, or may provide a separate display part to cause it to display an operation image. Further, the operation control part 32 may perform the operational control and the setting of various conditions of the first light source 12, the second light source 13, the optical connector 18, the interference light detection part 20, the optical path length, and the detection parts 30*a* and 30*b*.

[OCT Probe]

Figure 3:
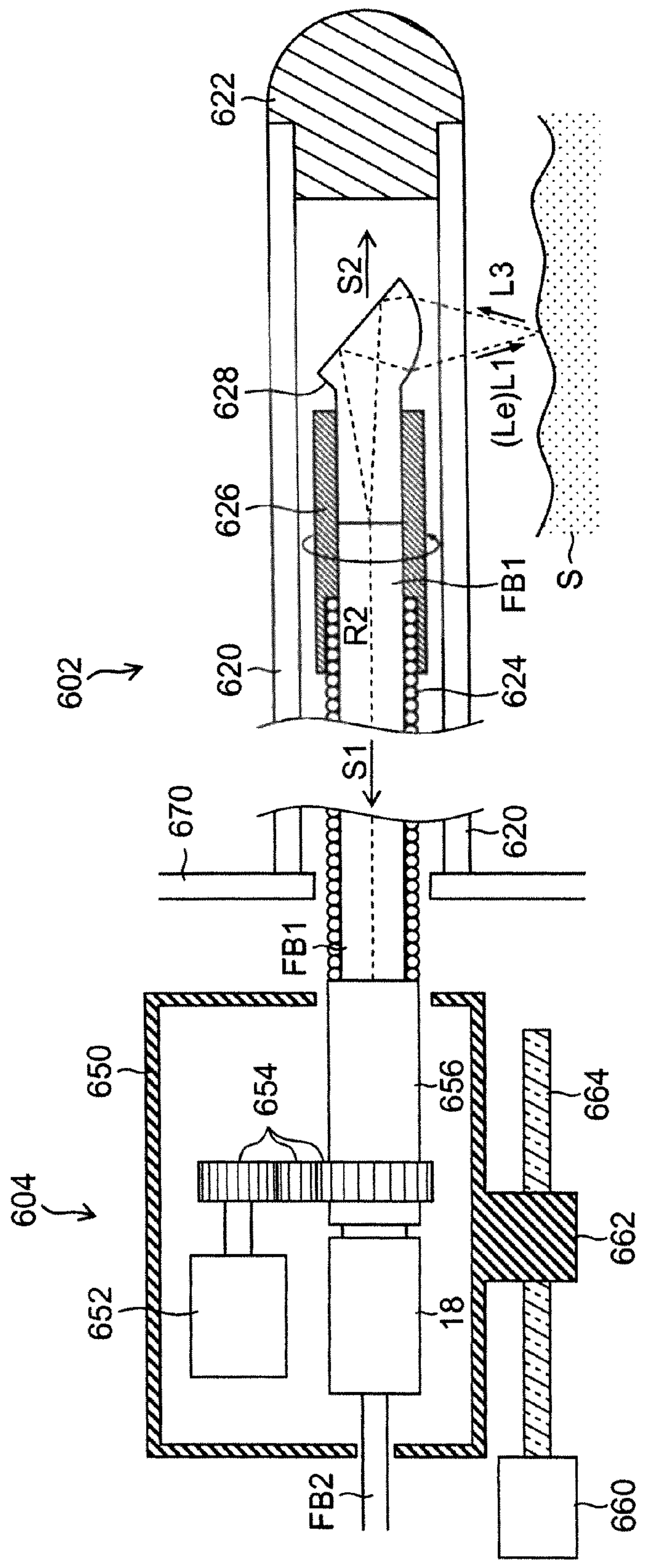
FIG. 3 is a sectional view of the OCT probe of FIG. 2.

FIG. 3 is a sectional view of the OCT probe of FIG. 2.

As shown in FIG. 3, the tip end part of the insertion part 602 includes a probe outer tube 620, a cap 622, a rotary-side optical fiber FB1, a spring 624, a fixing member 626, and an optical lens 628.

The probe outer tube (sheath) 620 is a flexible tubular member and is made of a material which allows the transmission of the sampling light L1 and the return light L3, which are combined with the aiming light L3 at the optical connector 18. It is noted that the probe outer tube 620 may be configured such that only a part thereof on the side of the tip end, through which the sampling light L1 (aiming light Le) and the return light L3 passes, is formed of a light permeable material (transparent material) all around the circumference, and the part other than the tip end may be formed of a light impermeable material.

The cap 622 is proved at the tip end of the probe outer tube 620 to close the tip end of the probe outer tube 620.

The rotary-side optical fiber FB 1, which is a wire member and is contained along the probe outer tube 620 within the probe outer tube 620, guides the sampling light L1 which is combined with the aiming light Le emitted from an optical fiber FB8 at the optical connector 18 to the optical lens 628, and guides the return light L3 from a measuring object S, which is acquired by the optical lens 628 by irradiating the sampling light L1 (aiming light Le) onto the measuring object S, to the optical connector 18, then making it enter into the fixed-side optical fiber FB2.

Here, the rotary-side optical fiber FB1 and the fixed-side optical fiber FB2 are optically connected by the optical connector 18 in such a state that the rotation of the rotary-side optical fiber FB1 is not transferred to the fixed-side optical fiber FB2. Further, the rotary-side optical fiber FB1 is disposed so as to be rotatable with respect to the probe outer tube 620 and movable in the axis direction of the probe outer tube 620.

The spring 624 is fixed to the outer periphery of the rotary-side optical fiber FB1. Further, the rotary-side optical fiber FB1 and the spring 624 are connected to the optical connector 18.

The optical lens 628 is disposed at the measuring-side tip end of the rotary-side optical fiber FB1 (the tip end of the rotary-side optical fiber FB1 opposite the optical connector 18), and the tip end part is formed into an approximately spherical shape so as to condense the sampling light L1 (aiming light Le) emitted from the rotary-side optical fiber FB1 toward the measuring object.

The optical lens 628 irradiates the sampling light L1 (aiming light Le) emitted from the rotary-side optical fiber FB 1 to the measuring object S and condenses the return light L3 from the measuring object S to make it enter into the rotary-side optical fiber FB1.

The fixing member 626 is disposed in the outer periphery of the connection part between the rotary-side optical fiber FB1 and the optical lens 628 to secure the optical lens 628 to the end part of the rotary-side optical fiber FB1. Here, the method of securing the rotary-side optical fiber FB1 and the optical lens 628 by the fixing member 626 is not specifically limited, and the fixing member 626 may be bonded with the rotary-side optical fiber FB1 and the optical lens 628 with an adhesive to be secured, or they may be secured with a mechanical structure using, for example, a bolt. It is noted that any types of fixing member 626 may be used provided they are intended to be used for securing, holding, or protecting optical fibers such as a zirconia ferrule and a metal ferrule.

Further, the rotary-side optical fiber FB1 and the spring 624 are connected to a rotary cylinder 656 which is to be described later, and the rotary-side optical fiber FB1 and the spring 624 is rotated by the rotary cylinder 656 so that the optical lens 628 is rotated in the arrow R2 direction with respect to the probe outer tube 620. Further, the optical connector 18 includes a rotary encoder and detects the irradiation position of the sampling light L1 from the position information (angle information) of the optical lens 628 based on the signal from the rotary encoder. That is, the measuring position is detected by detecting the angle with respect to a reference position in the rotation direction of the optical lens 628 which is rotating.

Further, the rotary-side optical fiber FB1, the spring 624, the fixing member 626, and the optical lens 628 are configured to be movable in the arrow S1 direction (forceps channel direction) and in the S2 direction (direction of the tip end of the probe outer tube 620).

Further, the left part of FIG. 3 is a schematic view of the driving part of the rotary-side optical fiber FB1 etc. in the operation part 604 of the OCT probe 600.

The probe outer tube 620 is secured to the fixing member 670. In contrast, the rotary-side optical fiber FB1 and the spring 624 are connected to the rotary cylinder 656, and the rotary cylinder 656 is configured to rotate via a gear 654 in response to the rotation of a motor 652. The rotary cylinder 656 is connected to the optical connector 18 and the sampling light L1 and the return light L3 are transmitted between the rotary-side optical fiber FB1 and the fixed-side optical fiber FB2.

Moreover, a frame 650 incorporating those includes a support member 662, which has a screw hole not shown in the figure. A ball screw 664 for advancing and retreating movement is in mesh with the screw hole, and a motor 660 is connected to the ball screw 664 for advancing and retreating movement. Thus, by driving the motor 660 in rotation thereby making the frame 650 advance and retreat, it is made possible to move the rotary-side optical fiber FB1, it is made possible to move the spring 624, the fixing member 626, and the optical lens 628 in the S1 and S2 directions of FIG. 3.

The OCT probe 600 has the configuration as described above in which the rotary-side optical fiber FB1 and the spring 624 are rotated in the arrow R2 direction so that the sampling light L1 (aiming light Le) emitted from the optical lens 628 is irradiated to the measuring object S while scanning in the arrow R2 direction (circumferential direction of the probe outer tube 620) to acquire the return light L3. The aiming light Le is irradiated to the measuring object S as a spot light of, for example, blue, red, or green color and the reflected light of the aiming light Le is also displayed as a bright spot on the observation image which is displayed on the monitor apparatus 500.

As the result of this, it is made possible to accurately capture a desired site of the measuring object S all around the circumference in the circumferential direction of the probe outer tube 620, and to acquire the return light L3 reflected from the measuring object S.

Further, when acquiring a plurality of optical structure information for generating an optical three-dimensional structure image, the optical lens 628 is moved to the terminal end of the movable range in the arrow S1 direction by the driving part, and is moved to the S2 direction by a predetermined amount each time while acquiring optical structure information made up of tomograms, or the optical structure information acquisition and the movement by a predetermined amount in the S2 direction are alternately repeated eventually moving to the end of the movable range.

Figure 4:
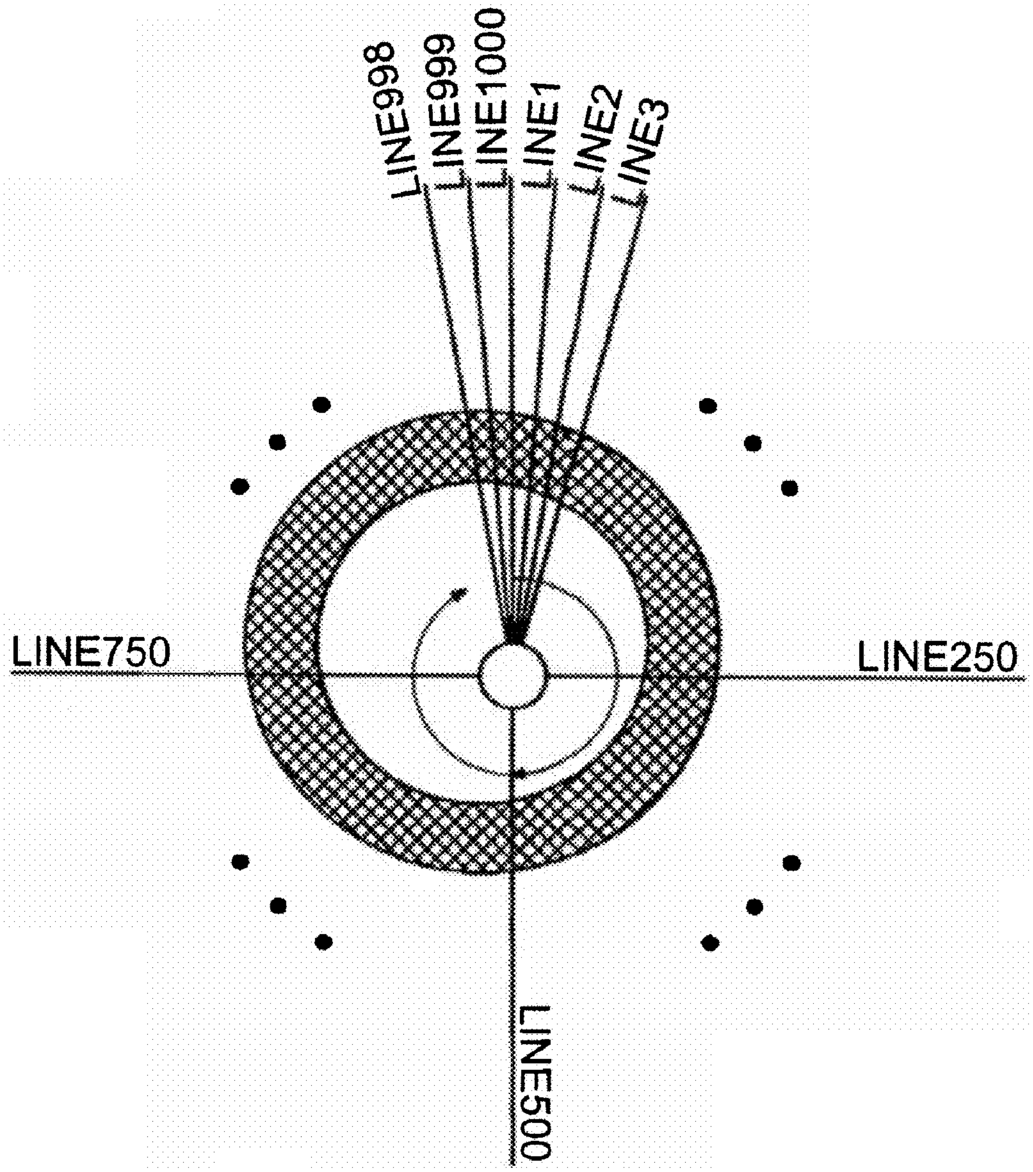
FIG. 4 shows a scanning plane of the structure information when optical scanning is a radial scanning for the measuring object S of FIG. 2.

Thus, it is possible to obtain a plurality of optical structure information within a desired range for the measuring object S and to obtain an optical three-dimensional structure image based on the acquired plurality of optical structure information. FIG. 4 shows a scanning plane of the optical structure information when optical scanning is a radial scanning for the measuring object S of FIG. 2, and FIG. 5 shows an optical three-dimensional structure image which is constructed from the optical structure information of FIG. 4.

Figure 5:
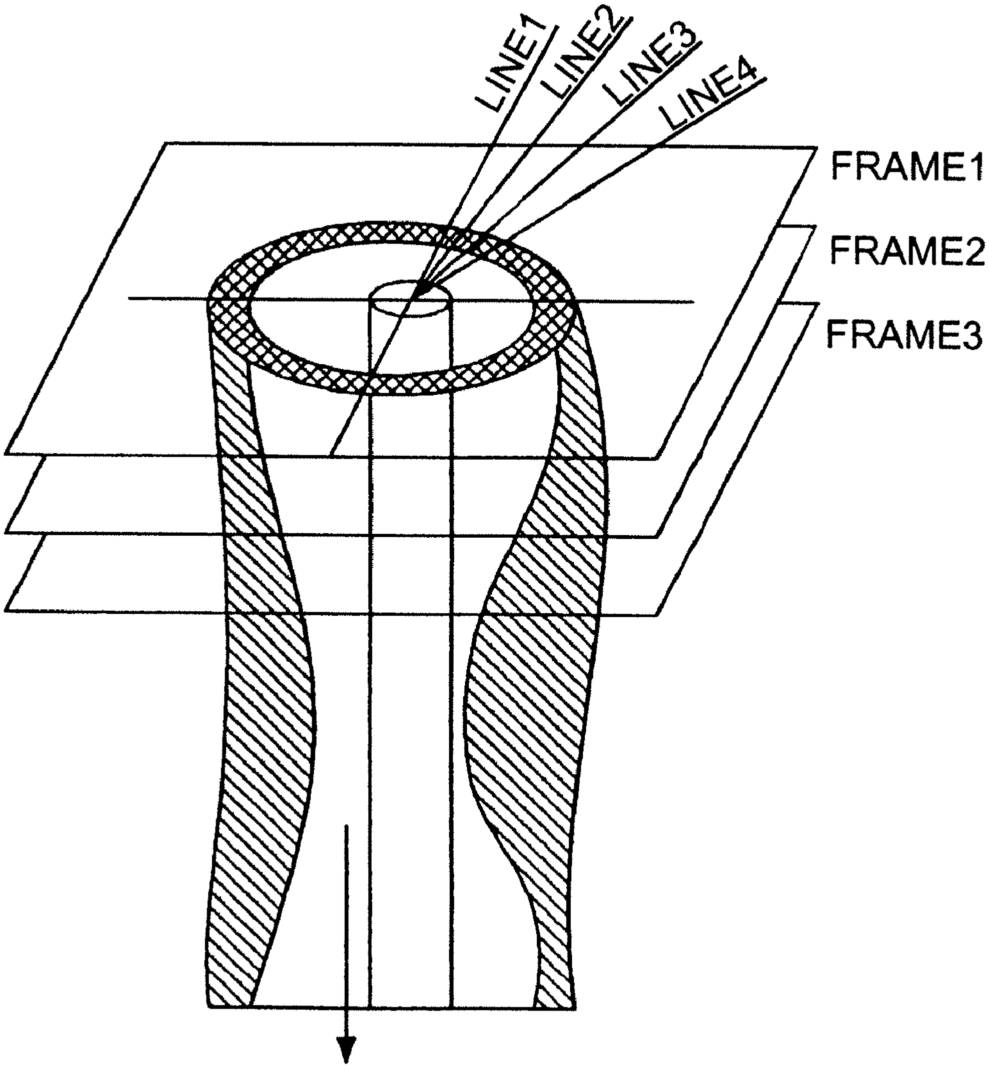
FIG. 5 shows a three-dimensional structure image which is constructed from the structure information of FIG. 4.

That is, by acquiring the optical structure information of the measuring object S in the depth direction (first direction) through interference signals and performing the scanning in the arrow R2 direction of FIG. 3 (the circumferential direction of the probe outer tube 620) for the measuring object S, it is made possible to acquire the structure information in the scanning plane made up of the first direction and the second direction which is perpendicular to the first direction, and further by moving the scanning plane along the third direction which is perpendicular to the scanning plane, it is made possible to acquire plurality of optical structure information for generating an optical three-dimensional structure image as shown in FIG. 5.

Figure 6:
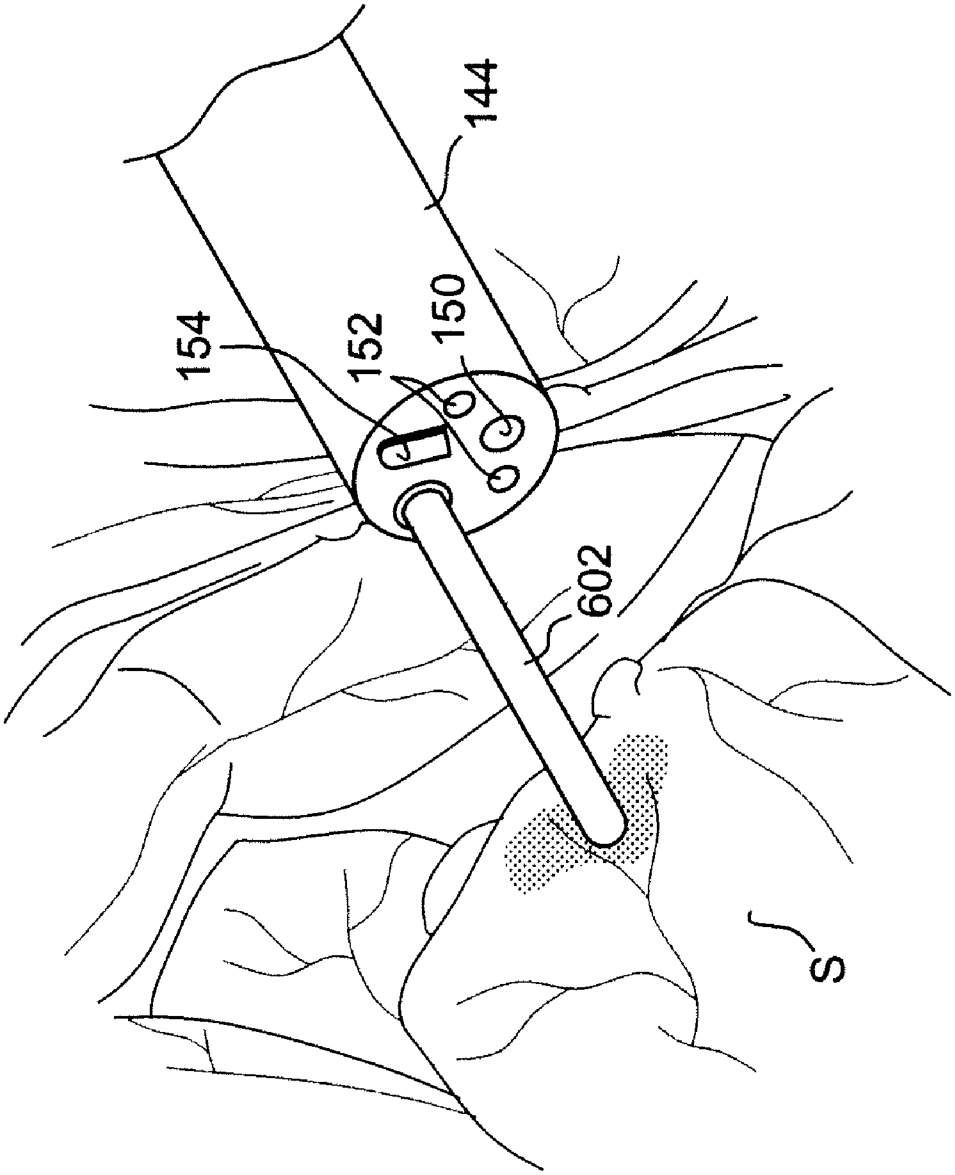
FIG. 6 shows the manner in which structure information is obtained using the OCT probe which is drawn out from a forceps channel of the endoscope of FIG. 1.

FIG. 6 shows the manner in which optical structure information is obtained using the OCT probe which is drawn out from a forceps channel of the endoscope of FIG. 1. As shown in FIG. 6, the tip end part of the insertion part 602 of the OCT probe is moved close to a desired site of the measuring object S to obtain optical structure information. When acquiring a plurality of optical structure information within a desired range, there is no need of moving the OCT probe 600 main body, and the optical lens 628 may be moved within the probe outer tube 620 by the above described driving part.

Figure 7:
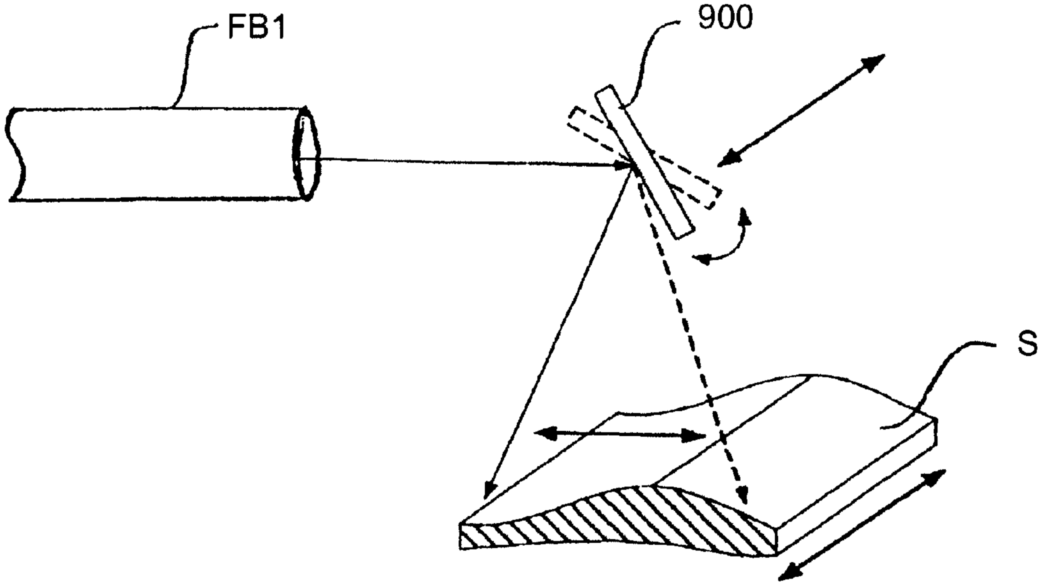
FIG. 7 shows a configuration for acquiring structure information by performing sector scanning against the measuring object S of FIG. 2.
Figure 8:
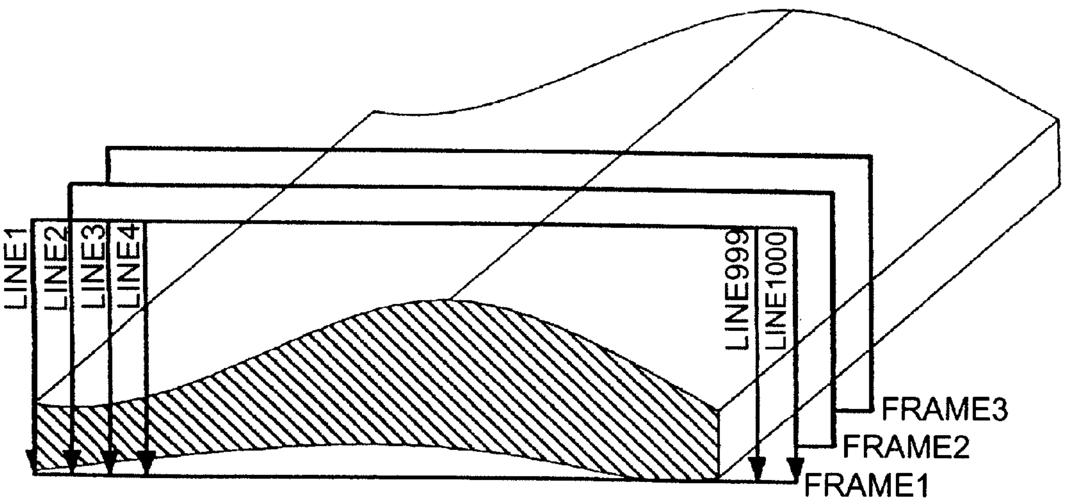
FIG. 8 shows a three-dimensional structure image which is constructed by the structure information of FIG. 7.

It is noted that although description has been made that the sampling light L1 (aiming light Le) is radially scanned against the measuring object S, this is not limiting. FIG. 7 shows a configuration for acquiring optical structure information by performing sector scanning against the measuring object S of FIG. 2; and FIG. 8 shows a three-dimensional structure image which is constructed with the structure information of FIG. 7. As shown in FIG. 7, a configuration in which a galvanometer mirror 900 is used to perform sector scanning from above the measuring object S thereby acquiring optical structure information can be applied, and in this case as well, by moving the scanning plane it is possible to acquire plurality of optical structure information to create an optical three-dimensional image as shown in FIG. 8.

[Interference Detection Part and Image Processing Part]

Figure 9:
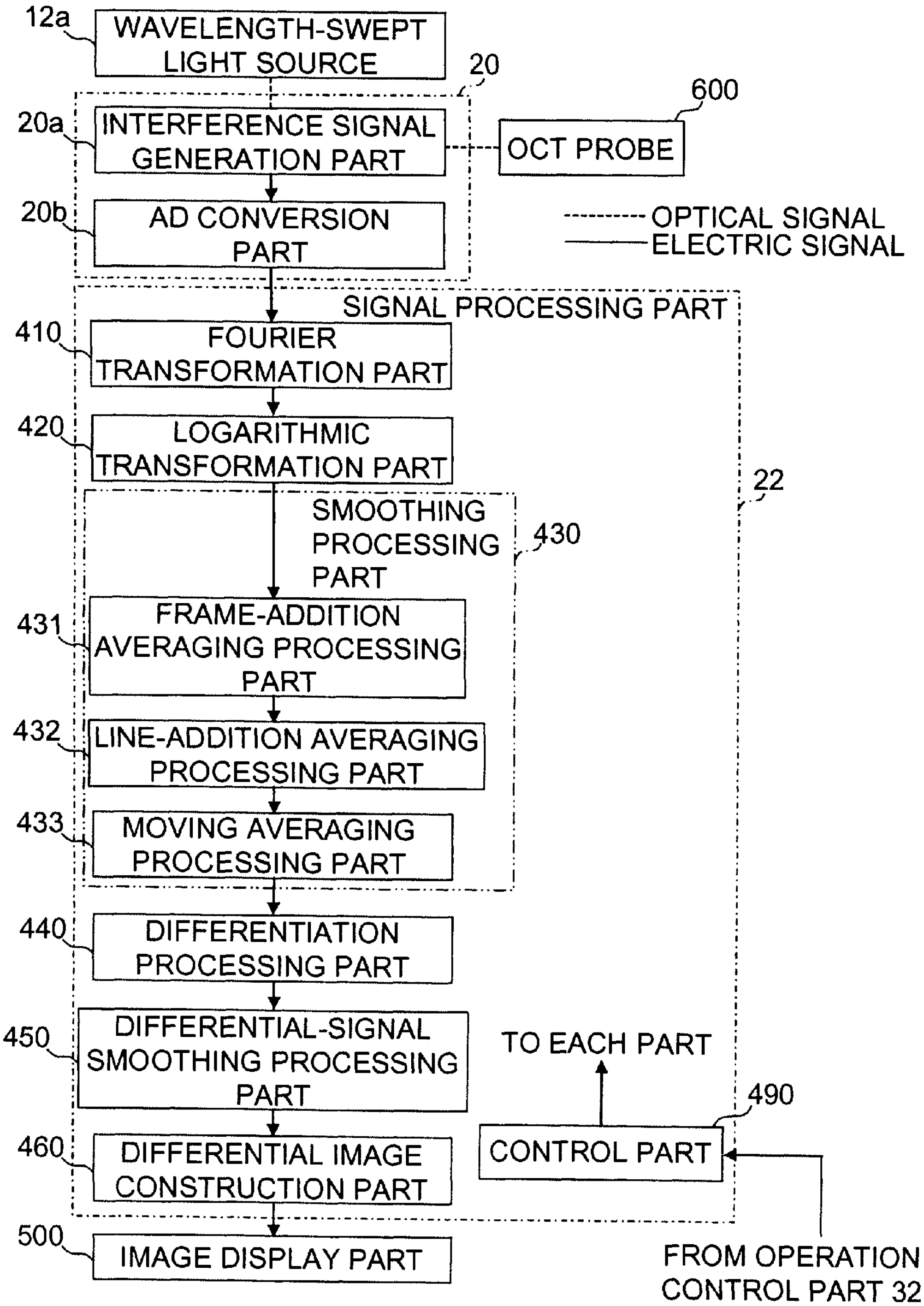
FIG. 9 is a block diagram to show the configurations of the interference light detection part and the signal processing part of FIG. 2.

FIG. 9 is a block diagram to show the configurations of the interference light detection part and the signal processing part of FIG. 2.

As shown in FIG. 9, the interference light detection part 20 is made up of an interference signal generation part 20*a* and an AD conversion part 20*b*. Moreover, the signal processing part 22 is made up of: a Fourier transformation part 410 as a layer information extraction device; a logarithmic transformation part 420 and a smoothing processing part 430 as a layer-information noise removal device; a differentiation processing part 440 as a feature value calculation device; a differential-signal smoothing processing part 450 as a feature-value noise removal device; and a differential image construction part 460 and a control part 490 as an enhanced layer-structure image construction device. It is noted that the control part 490 is adapted to control each part of the signal processing part 22 based on the operation signal from the operation control part 32.

The interference signal from the interference signal generation part 20*a* is made to be digital data at an AD conversion part 20*b*. The digitized interference signal is subjected to FFT (fast Fourier transformation) at the Fourier transformation part 410 and is frequency-decomposed to generate structure information (layer information) which is reflection intensity data in the depth direction. The optical structure information (layer information) which is the reflection intensity data in the depth direction is subjected to logarithmic transformation at a logarithmic transformation part 420.

While in a conventional OCT, logarithmically transformed optical structure information is subjected to brightness and contrast adjustment, resampling to fit to display size, and coordinate transformation in accordance with the scanning method such as radical scanning and sector scanning, etc., and is outputted as a tomographic image; in the present embodiment, the logarithmically transformed optical structure information is subjected to smoothing processing at a smoothing processing part 430.

The smoothing processing part 430 may be made up of solely a three-dimensional smoothing filter part or a two-dimensional smoothing filter part, or a combination of one-dimensional filter parts; it is preferably made up of a combination of one or more of a frame-averaging processing part 431, a line-averaging processing part 432, and a moving averaging processing part 433.

The frame-averaging processing part 431 performs smoothing by averaging the data between frames. In this occasion, although any one of simple frame averaging, weighted frame averaging, and recursive frame correlation is preferable, any generally known method may be applied. Also, there is no limitation on the number of frames which are subjected to averaging. The above described recursive frame correlation generates a frame data which combines new input frame data with current output frame data at a ratio of $\alpha:1-\alpha$ for output. Since it can be realized by securing frame memory for one frame, it can be advantageously realized with less memory compared with the frame averaging.

$$[OUT(n)]=\alpha\times[IN]+(1-\alpha)\times[OUT(n-1)]\ (\alpha\leqq 1) \qquad \text{(Eq. 1)}$$

Here, OUT(n) is the n-th output frame data, IN is a new input frame data, OUT(n−1) is the (n−1)-th output frame data, that is, the output frame data of the immediately preceding frame, and α is a frame correlation coefficient.

The line-averaging processing part 432 performs smoothing by averaging data between scanning lines. In this case as well, although simple averaging and weighted averaging are preferable, any generally known configuration may be used. The number of lines which are subjected to averaging is not specifically limited as well.

The moving averaging processing part 433 performs smoothing by averaging data in the depth direction. In this occasion, although any one of simple moving averaging, weighted moving averaging, and digital lowpass filtering is preferable, any generally known configuration may be used. Moreover, the number of data points to be averaged is not specifically limited.

Further, since even when the order of the above described logarithmic transformation part 420 and the above described smoothing processing part 430 is reversed, the same effect will be achieved and therefore the order is interchangeable.

The differentiation processing part 440 performs differentiation of the smoothed data in the depth direction to acquire a differential signal as a feature value. Since the differentiation processing is generally known, although it is not specifically limited, one example includes a method of calculating the difference for each data point in the depth direction.

A differential-signal smoothing processing part 450 performs smoothing processing on the differential signal (feature value). The differential-signal smoothing processing part 450 performs smoothing by averaging the differential signals in the depth direction. In this case as well, although any one of simple moving averaging, weighted moving averaging, and digital lowpass filtering is preferable, any generally known method may be used. Similarly, the number of data points to be averaged is not specifically limited.

The differential image construction part 460 constructs a differential image as an enhanced layer-structure image from the smoothed differential signal in accordance with the monitor apparatus 500 and the display method thereof. Specifically, a differential image is constructed by adjustment of brightness and contrast, resampling to fit to display size, and coordinate transformation in accordance with the scanning method such as radical scanning, and sector scanning, etc., and the like.

Further, preferably, in the differential image construction part 460, by extracting and imaging only plus components exceeding a predetermined threshold, for example, zero, of the smoothed differential signals to construct a differential image, it becomes possible to more clearly visualize layer structures such as a muscularis mucosa. Further, by turning the differential image into a color image by means of a predetermined color map, it becomes possible to make the target structure more recognizable. The constructed differential image will be displayed on a monitor apparatus 500 such as an LCD monitor and CRT monitor, etc. so as to be applied to diagnosis.

Figure 10:
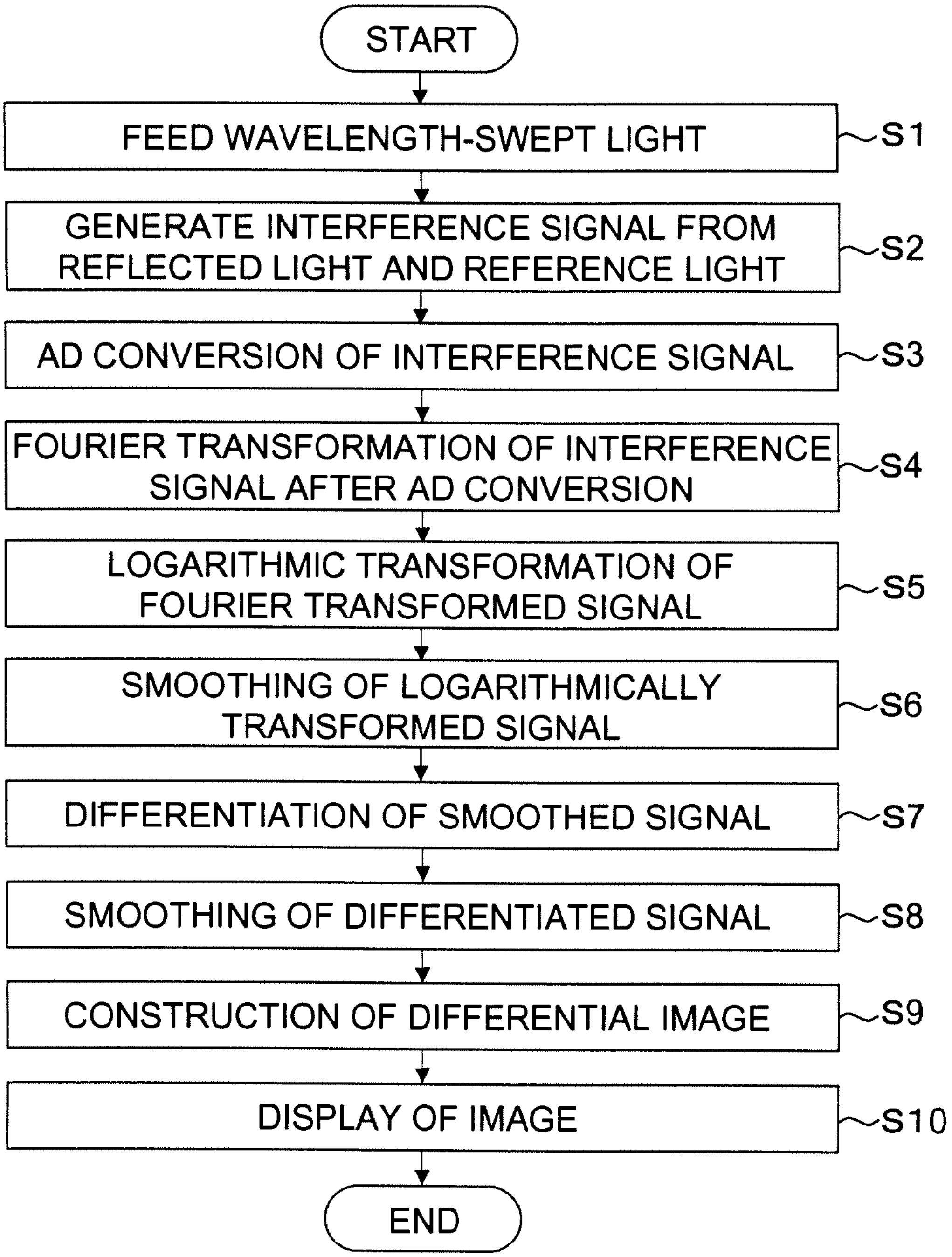
FIG. 10 is a flowchart to show the flow of processing in the interference light detection part and the signal processing part of FIG. 9.

The action of thus configured present embodiment will be described with reference to the flowchart of FIG. 10. FIG. 10 is a flowchart to show the flow of processing in the interference light detection part and the signal processing part of FIG. 9.

As shown in FIG. 10, first a wavelength-swept light outputted from a wavelength-swept light source 12*a* is branched into a sampling light and a reference light, and the sampling light is outputted to a measuring object S such as a living tissue through an OCT probe 600 (step S1). The reflected sampling light (return light) reflected by backscattering etc. at the measuring object S is inputted into an interference signal generation part 20*a* via the OCT probe 600. The interference signal generation part 20*a* generates an interference light between the reference light, which is reflected by an optical mirror, etc. disposed at an approximately same optical path length to the subject in the sampling light path, and the reflected sampling light, and subject the interference light to photoelectric conversion to generate an interference signal (step S2).

The interference signal is subjected to analog-to-digital conversion at an AD conversion part 20*b* (step S3). Although the AD conversion is performed at a sampling rate of, for example, about 80 MHz and a resolution of, for example, about 14 bit, these values are not limiting.

The signal processing part 22 performs Fourier transformation of the digitized interference signal at a Fourier transformation part 410 to provide a reflection intensity signal (layer information) in the depth direction (step S4). The reflection intensity signal is subjected to logarithmic transformation at a logarithmic transformation part 420 (step S5).

The logarithmically transformed reflection intensity data in the depth direction is smoothed at a smoothing processing part 430 (step S6). The smoothing processing performed at this occasion is preferably a combination of one or more of frame averaging, line averaging, and moving averaging processing. In that case, although the frame averaging is preferably any one of simple averaging, weighted averaging, and recursive frame correlation processing, other generally known methods may be used. Further, although the line averaging is preferably one of simple averaging and weighted averaging, other generally available approach may be adopted. Furthermore, although moving averaging is preferably any one of simple averaging, weighted averaging, and one-dimensional lowpass filtering, etc., another generally known method may be used. Further, although optimization is carried out as a combination of one-dimensional smoothing processing, it is possible to adopt a two-dimensional smoothing filter alone, or a combination of one-dimensional filters, or three-dimensional smoothing filtering.

The smoothed signal is differentiated at a differentiation processing part 440 (step S7). The differential signal (feature value) resulting from differentiation is smoothed in the depth direction at the differential-signal smoothing processing part 450 (step S8). In this case as well, although any one of simple moving averaging, weighted moving averaging, and digital lowpass filtering is preferable, any generally known processing may be used.

The differential image construction part 460 constructs a differential image from the smoothed differential signal in accordance with the monitor apparatus 500 and the display method thereof (step S9). Specifically, adjustments of brightness and contrast, resampling in accordance with display size, and coordinate transformation in accordance with the scanning method such as radial scanning and sector scanning, etc. are performed. Moreover, preferably, in the differential image construction part 460, by extracting only plus components of the smoothed differential values to construct a differential image, it becomes possible to more clearly visualize a layer structure such as a muscularis mucosa. Further, by turning a differential image into a color image according to a predetermined color map, it becomes possible to make the target structure more recognizable. The constructed differential image is displayed on the monitor apparatus 500 such as an LCD monitor and CRT monitor, etc (step S10).

Figure 11:
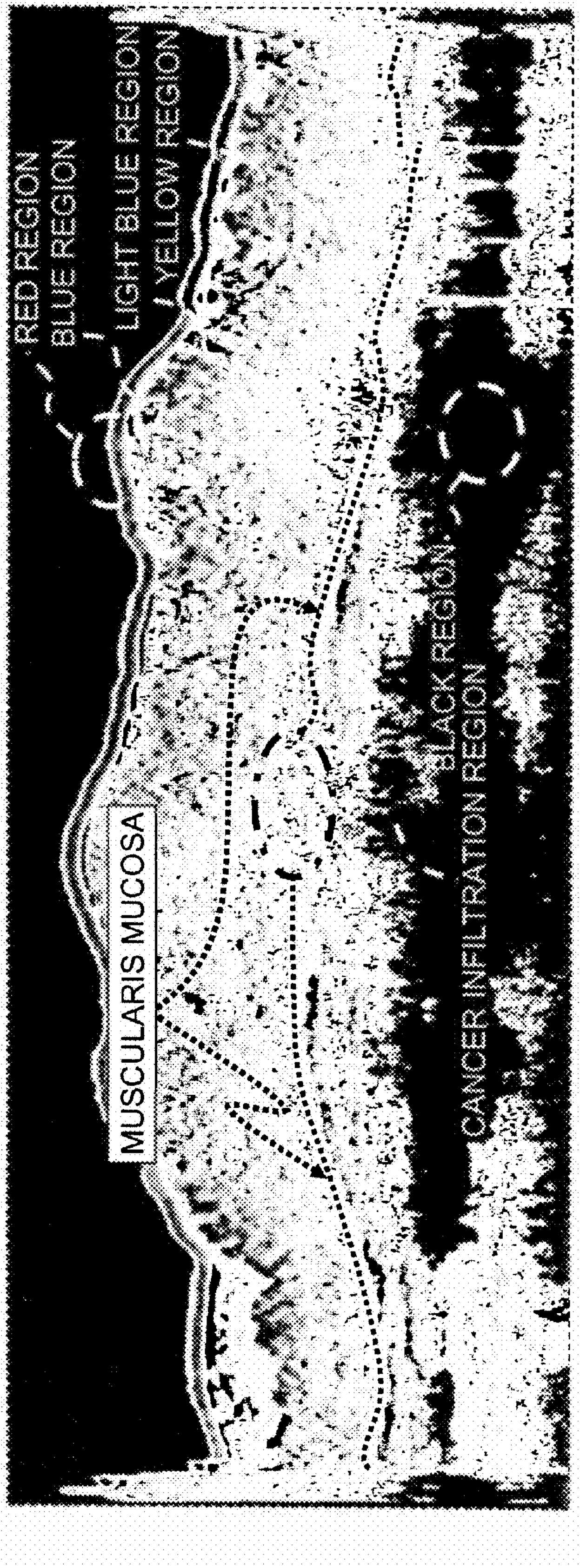
FIG. 11 shows a differential image (enhanced layer-structure image) generated by the signal processing part of FIG. 2.

FIG. 11 shows a differential image (enhanced layer-structure image) generated by the signal processing part of FIG. 2, in which a galvanometer mirror 900 is used to perform sector scanning from above the measuring object S thereby acquiring optical structure information, which is subjected to simple averaging of for example 8 frames at a frame-averaging processing part 431, simple averaging of, for example, 8 lines at a line-averaging processing part 432, simple moving averaging of, for example, 21 points at a moving averaging processing part 433, and simple moving averaging of, for example, 11 points at a differential-signal smoothing processing part 450. Further, the differentiation processing part 440 acquires differential signals by taking differences in the depth direction.

Further, although it cannot be discerned in FIG. 11, the differential image construction part 160 adopts a color map, in which the color changes from light blue to blue to ultramarine blue where the differential signal is negative, and changes from yellow to orange, to red, and to crimson. The yellow line (dotted line in the figure) shown in the middle layer of the differential image indicates a muscularis mucosa, and a broken part in the central region is a site in which the muscularis mucosa is destroyed by the infiltration of cancer. In this way, it becomes possible to visualize the muscularis mucosa.

Figure 12:
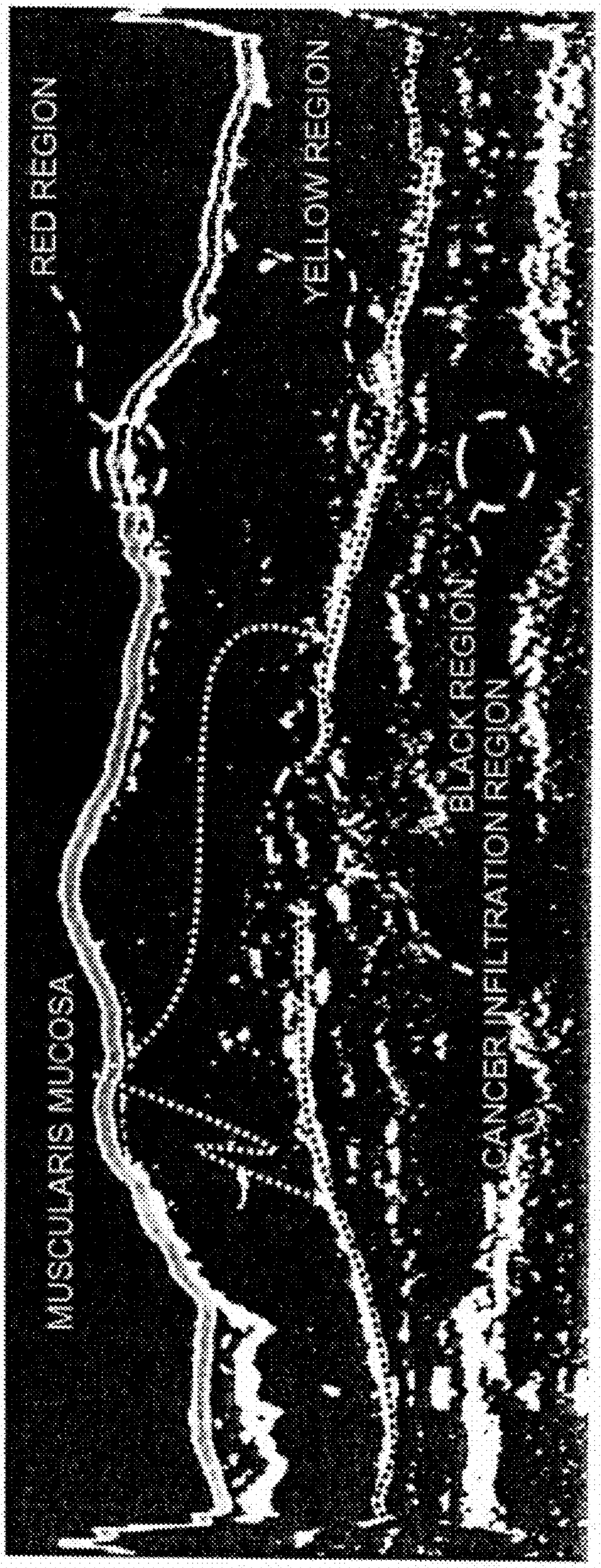
FIG. 12 shows a modification example of the differential image of FIG. 11.

FIG. 12 shows a modification example of the differential image of FIG. 11, which is a differential image in which only positive components of differential signals are extracted at the differential image construction part 460 and applied with a color map which changes from black to yellow, to orange, to red, and to crimson. Compared with the differential image of FIG. 11, the differential image of FIG. 12 has visualized a muscularis mucosa more clearly.

Second Embodiment

Figure 13:
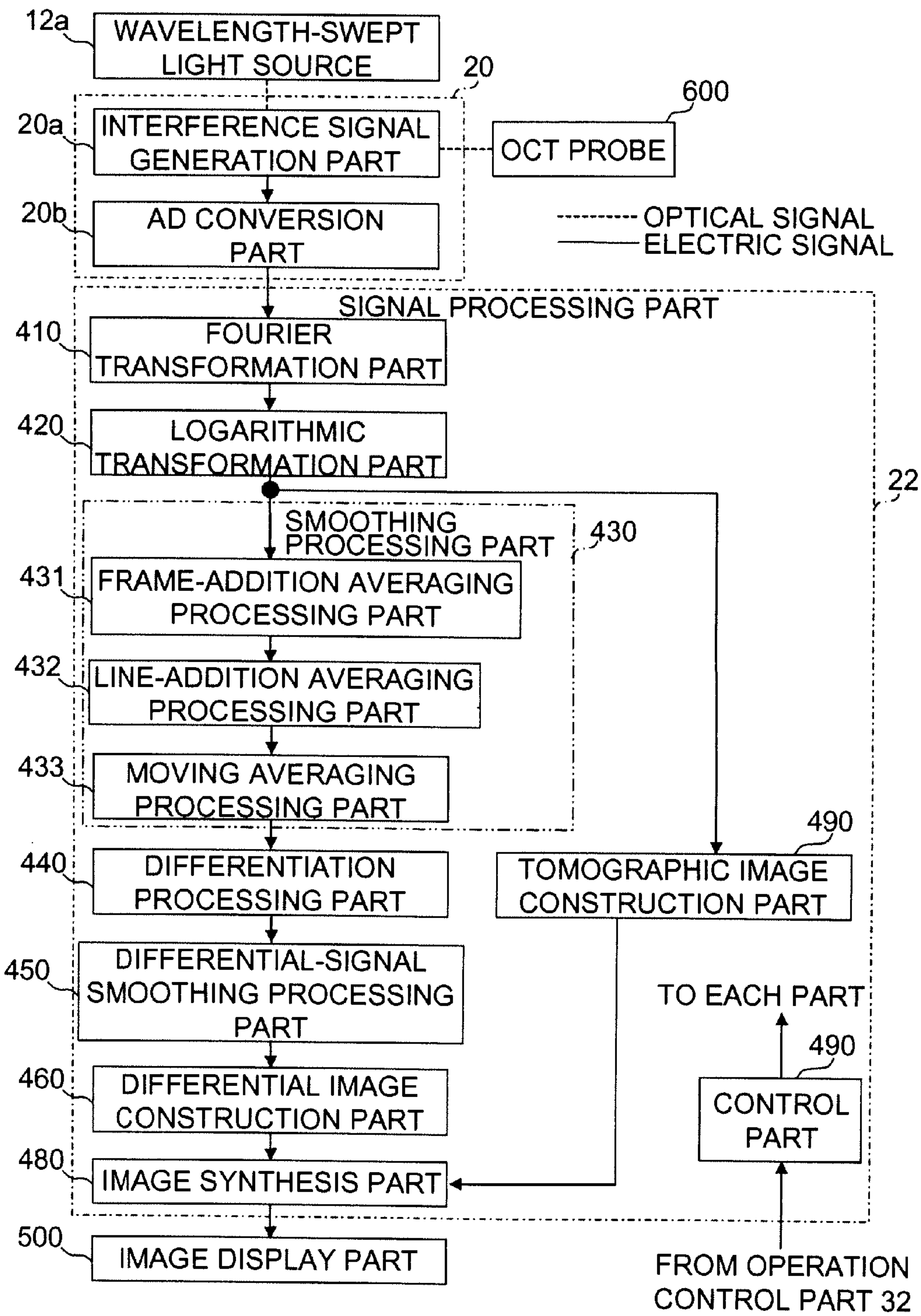
FIG. 13 is a block diagram to show the configuration of a signal processing part relating to a second embodiment.

FIG. 13 is a block diagram to show the configuration of a signal processing part relating to a second embodiment of the present invention. Since the present embodiment is almost same as the first embodiment, only the different configurations will be described and like components are given like reference symbols thereby omitting the description thereof.

As shown in FIG. 13, the signal processing part 22 includes a tomographic image construction part 470 and an image synthesis part 480 in addition to the configurations of the first embodiment.

The data which is logarithmically transformed at the logarithmic transformation part 420 is inputted to the smoothing processing part 430 as well as to the tomographic image construction part 470 to be constructed into an image in accordance with the monitor apparatus 500 and the display method thereof. Here, the image construction involves adjustments of brightness and contrast, application of color map, resampling in accordance with display size, coordinate transformation in accordance with the scanning method such as radial scanning and sector scanning etc., and the like.

The image constructed at the tomographic image construction part 470 and the image constructed at the differential image construction part 460 are synthesized at an image synthesis part 480 to be outputted to the monitor apparatus 500. The image synthesis method at the image synthesis part 480 is preferably a method of adding together and synthesizing a tomographic image and a differential image at a predetermined proportion. Specifically, there are:

(1) Method of adding a differential image at a fixed proportion β with the proportion of the tomographic image being 1, or $$\text{Synthesis image} = \text{Tomographic image} + \beta \times \text{Differential image } (0<\beta<1)$$

(2) Method of adding the both at a fixed proportion.

$$\text{Synthesis image} = (1-\alpha) \times \text{Tomographic image} + \beta \times \text{Differential image } (0<\beta<1)$$

However, the synthesis of images will not be limited to these methods, and any generally used method such as a method of superimposing a differential image onto a tomographic image may be used. The image outputted from the image synthesis part is disposed on the monitor apparatus 500 such as an LCD monitor thereby enabling the user to carry out diagnosis.

Figure 14:
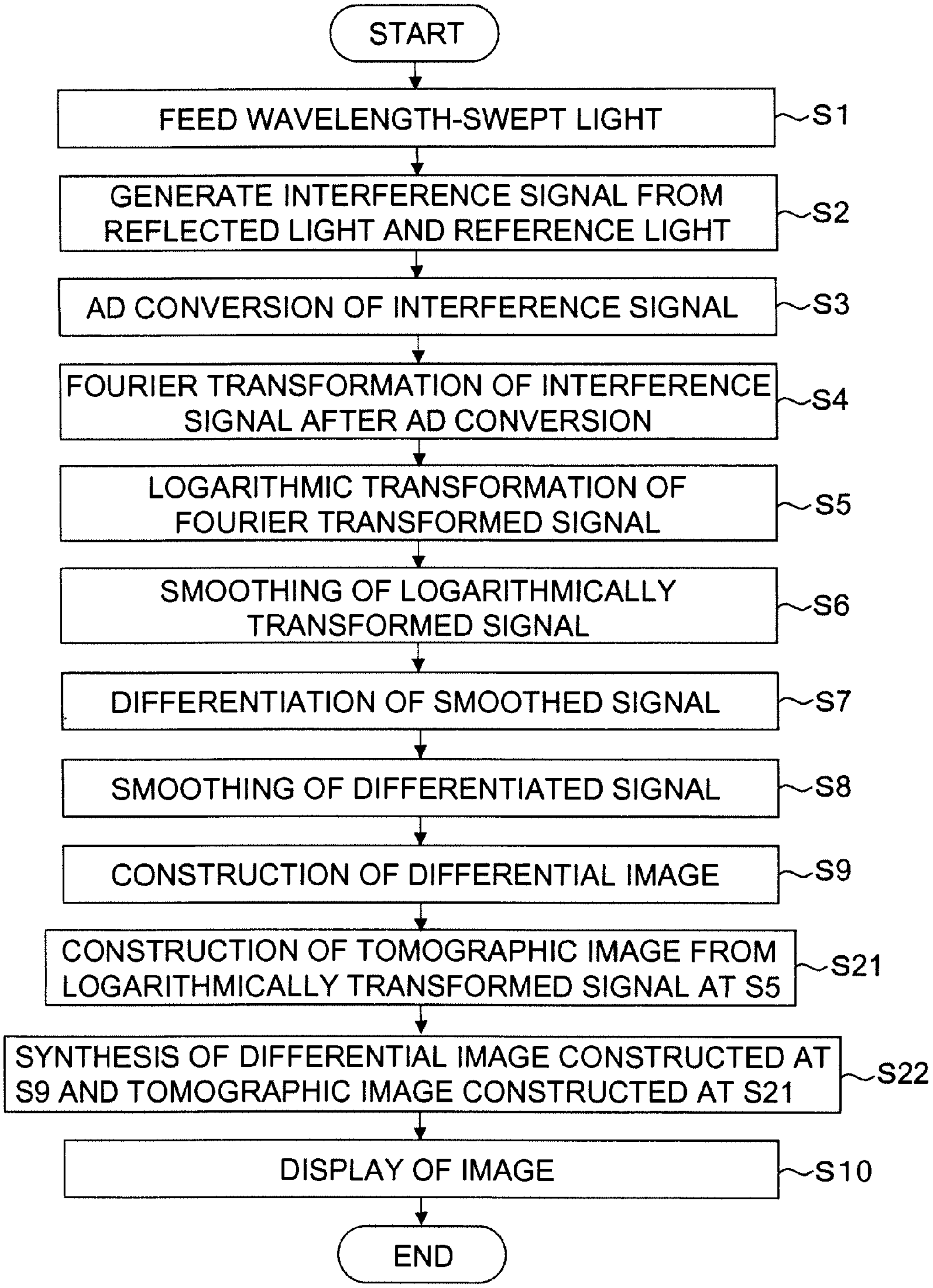
FIG. 14 is flowchart to show the flow of processing at the signal processing part of FIG. 13.

The action of the present embodiment, which is configured as described above, will be described using the flowchart of FIG. 14. FIG. 14 is a flowchart to show the flow of processing at the signal processing part of FIG. 13. The part of the flow of processing different from that of the first embodiment will be described.

The logarithmically transformed data generated at step S5 is inputted to the tomographic image construction part 470 so that a tomographic image is constructed (step S21). The differential image constructed at step S9 and the tomographic image constructed at step S21 are synthesized at the image synthesis part 480 (step S22).

The image synthesis method is preferably such that a tomographic image and a differential image are added together and synthesized at a predetermined proportion. Specifically, as described above, there are:

(1) Method of adding a differential image at a fixed proportion p with the proportion of the tomographic image being 1, or $$\text{Synthesis image} = \text{Tomographic image} + \beta \times \text{Differential image } (0<\alpha<1)$$

(2) Method of adding the both at a fixed proportion.

$$\text{Synthesis image} = (1-\alpha) \times \text{Tomographic image} + \beta \times \text{Differential image } (0<\beta<1)$$

However, the synthesis of images will not be limited to these methods, and any generally used method such as a method of superimposing a differential image onto a tomographic image may be used. The image synthesized by image synthesis is displayed on the monitor apparatus 500 such as an LCD monitor and a CRT monitor (step S10).

Figure 15:
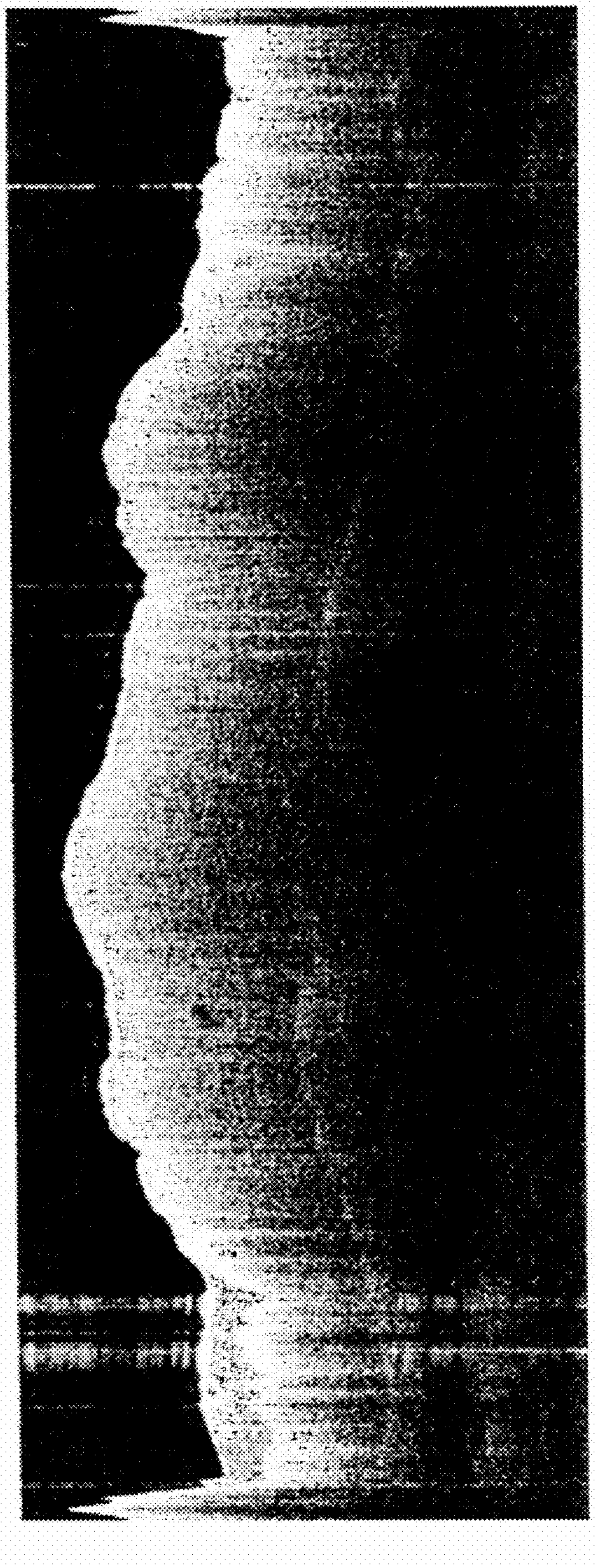
FIG. 15 shows a tomographic image constructed at the tomographic image construction part of FIG. 13.

FIG. 15 shows a tomographic image constructed at the tomographic image construction part of FIG. 13. This is of the same type as a gray scale tomographic image obtained by the signal processing of a conventional OCT, that is a tomography image constructed at the tomographic image construction part 470 for the optical structure information (layer information) which is acquired by performing sector scanning from above the measuring object S using a galvanometer mirror 900 described in FIG. 7.

Figure 16:
FIG. 16 shows a synthesis image generated by the image synthesis part of FIG. 13.

FIG. 16 shows a synthesis image generated by the image synthesis part of FIG. 13. The image shown in FIG. 16 is a synthesized image in which at the image synthesis part 480, with a proportion of the tomographic image (see FIG. 15) being 1, 0.2 proportion of the differential image constructed at the differential image construction part 460 is added thereto. By displaying in this way, the information of muscularis mucosa is added to an ordinary tomographic image so that it becomes easy to make judgment on whether cancer has infiltrated into the muscularis mucosa.

It is noted that although, in the above described each embodiment, description has been made on an S-OCT (Swept Source OCT) apparatus as the OCT processor 400, which is not limiting and the OCT processor 400 may be applied as an SD-OCT (Spectral Domain OCT) apparatus as well.

Using each above described embodiment of the present invention will enable users to clearly identify the muscularis mucosa, and thereby easily recognize if cancer has infiltrated into the muscularis mucosa layer. Therefore, selection of treatment methods will become easy.

Although, so far the optical apparatus for acquiring structure information of the present invention have been described in detail, the present invention will not be limited to the above described examples and, of course, various improvements and modifications may be made without departing from the scope of the present invention.

What is claimed is:

1. An optical apparatus for acquiring structure information comprising:

an optical branching device which splits a light outputted from a wavelength-swept light source into a sampling light and a reference light;

a scanning device which scans a subject having a layer structure with the sampling light; and an signal processing device which acquires optical structure information of the subject by processing an interference signal between a return light which is reflected or backscattered at the subject and the reference light which has propagated a predetermined optical path length;

wherein the signal processing device includes:

a layer information extraction device which extracts layer information of the subject based on the interference signal;

a feature value calculation device which calculates a feature value of the layer information; and an enhanced layer-structure image construction device which constructs an enhanced layer-structure image in which the layer structure is enhanced based on the feature value.

2. The optical apparatus for acquiring structure information according to claim 1, wherein the layer information extraction device is made up of a Fourier transformation device which performs Fourier transformation of the interference signal to extract the layer information, and the feature value calculation device is made up of a differentiation processing device which calculates a differential value resulting from differentiation of the layer information, as the feature value.

3. The optical apparatus for acquiring structure information according to claim 2, further comprising:

a layer-information noise component removal device which removes a noise component of the layer information; and a feature-value noise component removal device which removes a noise component of the feature value, wherein the differentiation processing device calculates a differential value resulting from the differentiation of the layer information from which the noise component is removed, as the feature value, and the enhanced layer-structure image construction device constructs the enhanced layer-structure image based on the feature value from which the noise component is removed.

4. The optical apparatus for acquiring structure information according to claim 3, wherein the layer-information noise component removal device is made up of a logarithmic-transformation smoothing device which performs logarithmic transformation and smoothing of the layer information to remove the noise component; and the feature-value noise component removal device is made up of a feature value smoothing processing device which performs smoothing of the feature value to remove the noise component.

5. The optical apparatus for acquiring structure information according to claim 4, wherein the logarithmic-transformation smoothing device performs smoothing of the layer information by at least any one of a frame averaging processing device, a line averaging processing device, and a moving averaging processing device.

6. The optical apparatus for acquiring structure information according to claim 5, wherein the frame averaging processing device performs averaging of the layer information between multiple frames by using any one of the processings of simple averaging, and weighted averaging, and recursive frame correlation.

7. The optical apparatus for acquiring structure information according to claim 5, wherein the line averaging processing device performs averaging of the signal between multiple lines by using one of the processes of simple averaging and weighted averaging.

8. The optical apparatus for acquiring structure information according to claim 5, wherein the moving averaging processing device performs smoothing of the signal in the depth direction by using any one of a simple moving average, a weighted moving average, and a lowpass filter.

9. The optical apparatus for acquiring structure information according to claim 4, wherein the feature value smoothing processing device performs smoothing of the feature value of the subject in the depth direction by using any one of a simple moving average, a weighted moving average, and a lowpass filter.

10. The optical apparatus for acquiring structure information according to claim 4, wherein the logarithmic-transformation smoothing device is made up of a logarithmic transformation device which performs logarithmic transformation of the layer information, and a smoothing device which performs smoothing of the logarithmically transformed layer information.

11. The optical apparatus for acquiring structure information according to claim 4, wherein the logarithmic-transformation smoothing device is made up of a smoothing device which performs smoothing of the layer information and a logarithmic transformation device which performs logarithmic transformation of the smoothed layer information.

12. The optical apparatus for acquiring structure information according to claim 4, wherein the enhanced layer-structure image construction device compares the feature value with a predetermined threshold and constructs an enhanced layer-structure image in which the layer structure is enhanced based on the comparison result.

13. The optical apparatus for acquiring structure information according to claim 4, wherein the enhanced layer-structure image construction device constructs an enhanced layer-structure image in which the layer structure is enhanced according to a predetermined color map, as a color image.

14. The optical apparatus for acquiring structure information according to claim 4, further comprising:

a layer-structure image construction device which constructs a layer structure image from the layer information which is logarithmically transformed by the logarithmic-transformation smoothing device, and an image synthesis device which synthesizes the layer structure image with the enhanced layer-structure image.

15. The optical apparatus for acquiring structure information according to claim 14, wherein the image synthesis device adds together and synthesizes the layer structure image with the enhanced layer-structure image at a predetermined proportion.

16. The optical apparatus for acquiring structure information according to claim 1, wherein the enhanced layer-structure image construction device compares the feature value with a predetermined threshold and constructs an enhanced layer-structure image in which the layer structure is enhanced based on the comparison result.

17. The optical apparatus for acquiring structure information according to claim 16, wherein the enhanced layer-structure image construction device constructs an enhanced layer-structure image in which the layer structure is enhanced according to a predetermined color map, as a color image.

18. A processing method of an optical interference signal of an optical apparatus for acquiring structure information comprising:

a light division step for splitting a light outputted from a wavelength-swept light source into a sampling light and a reference light;

a scanning step for scanning a subject having a layer structure with the sampling light; and a signal processing step for acquiring optical structure information of the subject by processing an interference signal between a return light which is reflected or backscattered at the subject and the reference light which has propagated a predetermined optical path length;

wherein the signal processing step includes:

a layer information extraction step for extracting the layer information of the subject based on the interference signal;

a feature value calculating step for calculating a feature value of the layer information; and an enhanced layer-structure image construction step for constructing an enhanced layer-structure image in which the layer structure is enhanced based on the feature value.

19. The processing method of an optical interference signal of an optical apparatus for acquiring structure information according to claim 18, wherein the layer information extraction step is made up of a Fourier transformation step for performing Fourier transformation of the interference signal to extract the layer information, and the feature value calculation step is made up of a differential processing step for calculating a differential value resulting from differentiation of the layer information, as the feature value.

20. The processing method of an optical interference signal of an optical apparatus for acquiring structure information according to claim 19, further comprising:

a layer-information noise component removal step for removing a noise component of the layer information; and a feature-value noise component removal step for removing a noise component of the feature value, wherein the differential processing step includes calculating a differential value resulting from the differentiation of the layer information from which the noise component is removed, as the feature value, and the enhanced layer-structure image construction step includes constructing the enhanced layer-structure image based on the feature value from which the noise component is removed.

21. The processing method of an optical interference signal of an optical apparatus for acquiring structure information according to claim 20, wherein the layer-information noise component removal step is made up of a logarithmic transformation smoothing step for performing logarithmic transformation and smoothing of the layer information to remove the noise component; and the feature-value noise component removal step is made up of a feature value smoothing processing step for performing smoothing of the feature value to remove the noise component.

22. The processing method of an optical interference signal of an optical apparatus for acquiring structure information according to claim 21, wherein the logarithmic transformation smoothing step performs smoothing of the layer information by at least any one of the steps of frame averaging processing, line averaging processing, and moving averaging processing.

23. The processing method of an optical interference signal of an optical apparatus for acquiring structure information according to claim 22, wherein the frame averaging processing step performs smoothing of the layer information between multiple frames by using any one of the processings of simple averaging, weighted averaging, and recursive frame correlation.

24. The processing method of an optical interference signal of an optical apparatus for acquiring structure information according to claim 22, wherein the line averaging processing step includes performing averaging of the signal between multiple lines by using one of the processings of simple averaging and weighted averaging.

25. The processing method of an optical interference signal of an optical apparatus for acquiring structure information according to claim 22, wherein the moving averaging processing step includes performing smoothing of the signal in the depth direction by using any one of a simple moving average, a weighted moving average, and a lowpass filter.

26. The processing method of an optical interference signal of an optical apparatus for acquiring structure information according to claim 21, wherein the feature value smoothing processing step includes performing smoothing of the feature value of the subject in the depth direction by using any one of a simple moving average, a weighted moving average, and a lowpass filter.

27. The processing method of an optical interference signal of an optical apparatus for acquiring structure information according to claim 21, wherein the logarithmic transformation smoothing step is made up of a logarithmic transformation step for performing logarithmic transformation of the layer information, and a smoothing step for performing smoothing of the layer information.

28. The processing method of an optical interference signal of an optical apparatus for acquiring structure information according to claim 21, wherein the logarithmic transformation smoothing step is made up of a smoothing step for performing smoothing of the layer information and a logarithmic transformation step for performing logarithmic transformation of the smoothed layer information.

29. The processing method of an optical interference signal of an optical apparatus for acquiring structure information according to claim 21, wherein the enhanced layer-structure image construction step includes comparing the feature value with a predetermined threshold and constructing an enhanced layer-structure image in which the layer structure is enhanced based on the comparison result.

30. The processing method of an optical interference signal of an optical apparatus for acquiring structure information according to claim 21, wherein the enhanced layer-structure image construction step includes constructing an enhanced layer-structure image in which the layer structure is enhanced according to a predetermined color map, as a color image.

31. The processing method of an optical interference signal of an optical apparatus for acquiring structure information according to a claim 21, further comprising:

a layer-structure image construction step for constructing a layer structure image from the layer information which is logarithmically transformed by the logarithmic transformation smoothing step, and an image synthesis step for synthesizing the layer structure image with the enhanced layer-structure image.

32. The processing method of an optical interference signal of an optical apparatus for acquiring structure information according to claim 31, wherein the image synthesis step includes adding together and synthesizing the layer structure image with the enhanced layer-structure image at a predetermined proportion.

33. The processing method of an optical interference signal of an optical apparatus for acquiring structure information according to claim 18, wherein the enhanced layer-structure image construction step includes comparing the feature value with a predetermined threshold and constructing an enhanced layer-structure image in which the layer structure is enhanced based on the comparison result.

34. The processing method of an optical interference signal of an optical apparatus for acquiring structure information according to claim 33, wherein the enhanced layer-structure image construction step includes constructing an enhanced layer-structure image in which the layer structure is enhanced according to a predetermined color map, as a color image.

* * * * *